United States Patent
Hönig et al.

(10) Patent No.: US 10,774,084 B2
(45) Date of Patent: Sep. 15, 2020

(54) ADENINE DERIVATIVES AND THEIR USE AS UV-PHOTOPROTECTIVE AGENTS

(71) Applicant: UNIVERZITA PALACKEHO V OLOMOUCI, Olomouc (CZ)

(72) Inventors: Martin Hönig, Cervenka (CZ); Lucie Plihalova, Olomouc (CZ); Karel Dolezal, Hlubocky (CZ); Jiri Voller, Brno-Bystrc (CZ); Miroslav Strnad, Olomouc (CZ); Lukas Spichal, Olomouc (CZ); Jitka Vostalova, Kozusany-Tazaly (CZ); Alena Rajnochova Svobodova, Olomouc (CZ); Jitka Ulrichova, Olomouc (CZ); Alena Kadlecova, Tvrdonice (CZ); Ondrej Plihal, Olomouc (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 15/753,828

(22) PCT Filed: Aug. 24, 2016

(86) PCT No.: PCT/CZ2016/050029
§ 371 (c)(1),
(2) Date: Feb. 20, 2018

(87) PCT Pub. No.: WO2017/036434
PCT Pub. Date: Mar. 9, 2017

(65) Prior Publication Data
US 2018/0298004 A1    Oct. 18, 2018

(30) Foreign Application Priority Data
Aug. 28, 2015 (CZ) .................. PV 2015-582

(51) Int. Cl.
| | | |
|---|---|---|
| *C07D 473/34* | (2006.01) | |
| *C07D 473/40* | (2006.01) | |
| *A61K 8/49* | (2006.01) | |
| *A61Q 17/04* | (2006.01) | |
| *A61K 31/52* | (2006.01) | |
| *A61Q 19/00* | (2006.01) | |
| *C07D 473/00* | (2006.01) | |
| *A01N 3/00* | (2006.01) | |
| *A01N 1/02* | (2006.01) | |

(52) U.S. Cl.
CPC .......... *C07D 473/34* (2013.01); *A01N 1/021* (2013.01); *A01N 3/00* (2013.01); *A61K 8/49* (2013.01); *A61K 31/52* (2013.01); *A61Q 17/04* (2013.01); *A61Q 19/00* (2013.01); *C07D 473/00* (2013.01); *C07D 473/40* (2013.01); *A61K 2800/522* (2013.01)

(58) Field of Classification Search
CPC ........................ C07D 473/34; A61K 31/522
See application file for complete search history.

(56) References Cited

U.S. PATENT DOCUMENTS

| | | |
|---|---|---|
| 2008/0009508 A1 | 1/2008 | Szucova et al. |
| 2009/0170879 A1 | 7/2009 | Szucova et al. |

OTHER PUBLICATIONS

Thompson et al. (J. Med. Chem., 1991, 34(9), pp. 2877-2882).*
Hasan et al. (Indian Journal of Chemistry, 1986, 25B, pp. 1070-1071).*
Thompson et al. (J. Med. Chem., 1991, 34, pp. 2877-2882).*
Vaclav Mik et al: N9-substituted derivatives of kinetin: Effective anti-senescence agents, Phytochemistry, vol. 72, No. 8, Feb. 2011, pp. 821-831.
Hasan A. et al: "Studies in Nucleosides Part XIV—Synthesis of 2-Chloro/Methoxy-6-N-Substituted-9-(2-Tetr Ahydrofuranyl)-9H-Purines & Theirbiological Activity",Indian Journal of Chemistry. Section B,Council of Scientific and Industrialresearch (C S I R), IN,vol. 25B, No. 10, Oct. 1986.
International Search Report and Written Opinion for PCT/CZ2016/050029 dated Aug. 28, 2016.

* cited by examiner

*Primary Examiner* — Susanna Moore
(74) *Attorney, Agent, or Firm* — Notaro, Michalos & Zaccaria P.C.

(57) ABSTRACT

Adenine derivatives substituted at the C2, N6, and N9 purine positions having antisenescent and combined photoprotective UVA/UVB effects. These substances are particularly suitable as anti-senescent and UV-photoprotective component in cosmetic preparations, plant protection preparations and in preparations for the treatment/application of tissue cultures.

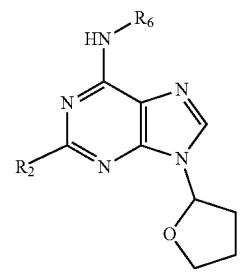

8 Claims, No Drawings

ADENINE DERIVATIVES AND THEIR USE AS UV-PHOTOPROTECTIVE AGENTS

FIELD OF INVENTION

The invention relates to adenine derivatives with combined anti-senescent and UV-photoprotective effects against UVA and UVB radiation. Further it relates to their use thereof.

BACKGROUND ART 6-furfurylaminopurine (kinetin) is a compound that belongs to plant hormone group called cytokinins. Cytokinins are structurally $N^6$-substituted adenine derivatives. Kinetin was discovered in 1950s and considered to be a growth regulator because it positively influenced the growth of tobacco callus cells. Exogenous application of kinetin induces cell differentiation and morphogenesis of the cells of plant callus and postpones the senescence of leaves. Except for the influence on plant cells, it shows also effects on animal cells. Kinetin possess antioxidant properties and is able to protect against oxidative stress—it is able to inhibit oxidation and damage of proteins, to influence the growth of keratinocytes and to delay aging of human skin fibroblasts in vivo although the compound does not influence proliferation of these fibroblasts. Kinetin derivative 6-furfurylamino-9-(2-tetrahydropyran-2-yl)purine (trade name Pyratine) that is currently commercially used in cosmetic preparations, was prepared by merging protective tetrahydropyranyl group with the kinetin molecule. This structural modification led to the improvement of anti-senescent and antioxidant effects on plant and animal cells including the tests performed on human skin or human skin models.

In recent years, increasing amounts of UV radiation (particularly the secondary (UVB) and long (UVA) wavelengths) reach the Earth's surface. This is a new phenomenon that contributes to the development of a number of skin diseases and disorders in humans. UVB radiation forms about 4-5% of the total radiation and is able to penetrate the skin and the epidermis, where it causes direct and indirect adverse biological effects. UVA accounts for 90% of the total proportion of radiation and penetrates deeper into the papillary dermis and partially into the hypodermis (10%), which causes the formation of reactive oxygen species (ROS) and reactive nitrogen species (RNS). Chronic skin exposure to UVA radiation can lead to premature aging of the skin, which is associated with structural damage of the dermis, resulting in the formation of wrinkles, moles and other signs of skin aging. Natural endogenous photoprotective agent is melanin, but it is not formed in sufficient amounts in human skin, particularly in relation to increasing intensity of UV radiation reaching the Earth due to ozone depletion in the atmosphere and lifestyle modifications (more outdoor activities, clothing that covers smaller part of the body surface). If the skin is treated with a substance which prevents penetration of UV rays in particular, it can protect against premature aging but also against short term adverse effects of UV radiation. Majority of products currently used in cosmetics to protect against solar radiation are so-called sunscreens (UV filters). These sunscreens were developed to protect skin primarily against "harmful" UVB radiation which may give rise to malignant melanokarcinoma. Sunscreens are divided into preparations with physical mechanism of action (inorganic minerals that create a physical barrier to radiation on the skin, such as TiO2 or ZnO) and preparations with chemical mechanism of action (organic substances capable to absorb the radiation by changing the distribution of electrons—for example benzophenones, cinnamate, salicylate). For some existing sunscreens, adverse reactions associated mainly with photoallergic or fotoirritating reactions have been reported when using these products. A common problem of these substances is also photo-instability.

The present inventors found a compound which unexpectedly combines antisenescence effects and UV-photoprotective effects (against both UVB and UVA radiation). These substances are very stable, they are not phototoxic and they do not irritate treated skin.

DISCLOSURE OF THE INVENTION

The invention relates to adenine derivatives of general formula I

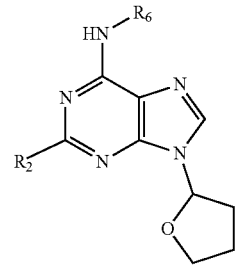

and pharmaceutically acceptable salts thereof with alkali metals, ammonia, amines, or addition salts with acids, wherein R2 is hydrogen or halogen;

R6 is selected from a group containing heteroaryl with 5- to 6-membered aromatic ring containing at least one heteroatom selected from O, S whereas other ring atoms are carbon atoms, while heteroaryl is unsubstituted or substituted by at least one substituent selected from the group consisting of C1-C4 alkyl, hydroxy(C1-C4)alkyl, mercapto(C1-C4)alkyl, formyl, acetyl, halogen, carboxyl, amino, di(C1-C4)alkylamino, amino(C1-C4)alkyl;

heteroarylalkyl with 5- to 6-membered aromatic ring containing at least one heteroatom selected from O, S whereas other atoms of the ring are carbon atoms, wherein the alkyl contains 1 to 4 carbon atoms, whereas the heteroarylalkyl is unsubstituted or substituted by at least one substituent selected from the group C1-C4 alkyl, hydroxy(C1-C4)alkyl, mercapto(C1-C4)alkyl, formyl, acetyl, halogen, carboxyl, amino, di(C1-C4) alkylamino, amino(C1-C4)alkyl;

heterocyclyl with 5- to 6-membered aliphatic ring containing at least one heteroatom selected from O, S whereas other atoms of the ring are carbon atoms, wherein the heterocycle is unsubstituted or substituted by at least one substituent selected from the group C1-C4 alkyl, hydroxy(C1-C4)alkyl, merkapto(C1-C4) alkyl, formyl, acetyl, halogen, carboxyl, amino, di(C1-C4)alkylamino, amino(C1-C4)alkyl;

heterocyclylalkyl with 5- to 6-membered aliphatic ring containing at least one heteroatom selected from O, S whereas other atoms of the ring are carbon atoms, the alkyl contains 1 to 4 carbon atoms, whereas the heterocyclylalkyl is unsubstituted or substituted by at least one substituent selected from the group C1-C4 alkyl, hydroxy(C1-C4)alkyl, mercapto(C1-C4)alkyl, formyl, acetyl, halogen, carboxyl, amino, di(C1-C4)alkylamino, amino(C1-C4)alkyl; cycloalkyl with ring containing 5 to 6 carbon atoms, unsubstituted or substituted by at least one substituent selected from the group C1-C4 alkyl, hydroxy(C1-C4)alkyl, mercapto(C1-C4)

alkyl, formyl, acetyl, halogen, carboxyl, amino, di(C1-C4)alkylamino, amino(C1-C4)alkyl;

cycloalkylalkyl with ring containing 5 to 6 carbon atoms, wherein the alkyl contains 1 to 4 carbon atoms, whereas the cycloalkylalkyl is unsubstituted or substituted by at least one substituent selected from the group containing C1-C4 alkyl, hydroxy(C1-C4)alkyl, mercapto(C1-C4) alkyl, formyl, acetyl, halogen, carboxyl, amino, di(C1-C4)alkylamino, amino(C1-C4)alkyl;

isoalkyl containing 3 to 7 carbon atoms, unsubstituted or substituted by at least one substituent selected from the group containing C1-C4 alkyl, hydroxy(C1-C4)alkyl, mercapto(C1-C4)alkyl, formyl, acetyl, halogen, carboxyl, amino, di(C1-C4)alkylamino, amino(C1-C4) alkyl.

Heteroalkyl preferably comprises a 5-membered ring, more preferably it contains one heteroatom in the 5-membered ring, said heteroatom being O or S. Most preferably, the heteroalkyl is furan-2-yl or thiophen-2-yl.

Heteroarylalkyl preferably comprises a 5-membered ring and a C1-C2 alkyl, more preferably it contains one heteroatom in the 5-membered ring, said heteroatom being O or S. Most preferably, the heteroarylalkyl is selected from furan-2-ylmethyl (furfuryl) and thiophen-2-ylmethyl.

Heterocyclyl preferably comprises a 5-membered ring, more preferably it contains one heteroatom in the 5-membered ring, said heteroatom being O or S. Most preferably, the heterocyclyl is selected from tetrahydrofuran-2-yl and tetrahydrothiophen-2-yl.

Heterocyclylalkyl preferably comprises a 5-membered ring and a C1-C2 alkyl, more preferably it contains one heteroatom, said heteroatom being O or S. Most preferably, the heterocyclylalkyl is selected from tetrahydrofuran-2-ylmethyl and tetrahydrothiophen-2-ylmethyl.

Cycloalkyl is preferably cyclopentyl. Cycloalkylalkyl is preferably cyclopentylmethyl.

Isoalkyl is preferably selected from isopropyl, isobutyl, isopentyl, isohexyl and isoheptyl.

Halogen is selected from the group comprising fluorine, chlorine, bromine and iodine, the most preferred halogen is chlorine.

Particularly preferred compounds of the invention are the compounds of formula I selected from the group consisting of
6-(tetrahydrofuran-2-ylmethylamino)-9-(tetrahydrofuran-2-yl)purine
6-(5-methylfuran-2-ylmethylamino)-9-(tetrahydrofuran-2-yl)purine
6-(5-hydroxymethylfuran-2-ylmethylamino)-9-(tetrahydrofuran-2-yl)purine
6-(5-formylfuran-2-ylmethylamino)-9-(tetrahydrofuran-2-yl)purine
6-(1-furan-2-ylethylamino)-9-(tetrahydrofuran-2-yl)purine
6-(5-methyltetrahydrofuran-2-ylmethylamino)-9-(tetrahydrofuran-2-yl)purine
6-(1-tetrahydrofuran-2-ylethylamino)-9-(tetrahydrofuran-2-yl)purine
6-(cyclopentylmethylamino)-9-(tetrahydrofuran-2-yl)purine
6-(thiophen-2-ylmethylamino)-9-(tetrahydrofuran-2-yl)purine
6-(3-methylthiophen-2-ylmethylamino)-9-(tetrahydrofuran-2-yl)purine
6-(5-methylthiophen-2-ylmethylamino)-9-(tetrahydrofuran-2-yl)purine
6-(5-chlorothiophen-2-ylmethylamino)-9-(tetrahydrofuran-2-yl)purine
6-(5-bromothiophen-2-ylmethylamino)-9-(tetrahydrofuran-2-yl)purine
6-(1-thiophen-2-ylethylamino)-9-(tetrahydrofuran-2-yl)purine
2-chloro-6-furfurylamino-9-(tetrahydrofuran-2-yl)purine
2-chloro-6-(5-methylfuran-2-ylmethylamino)-9-(tetrahydrofuran-2-yl)purine
2-chloro-6-(5-hydroxymethylfuran-2-ylmethylamino)-9-(tetrahydrofuran-2-yl)purine
2-chloro-6-(5-formylfuran-2-ylmethylamino)-9-(tetrahydrofuran-2-yl)purine
2-chloro-6-(1-furan-2-ylethylamino)-9-(tetrahydrofuran-2-yl)purine
2-chloro-6-(tetrahydrofuran-2-ylmethylamino)-9-(tetrahydrofuran-2-yl)purine
2-chloro-6-(5-methytetrahydrfuran-2-yl)purine
2-chloro-6-(1-tetrahydrofuran-2-ylethylamino)-9-(tetrahydrofuran-2-yl)purine
2-chloro-6-(thiophen-2-ylamino)-9-(tetrahydrofuran-2-yl)purine
2-chloro-6-(thiophen-2-ylmethylamino)-9-(tetrahydrofuran-2-yl)purine
2-chloro-6-(3-methylthiophen-2-ylmethylamino)-9-(tetrahydrofuran-2-yl)purine
2-chloro-6-(5-methylthiophen-2-ylmethylamino)-9-(tetrahydrofuran-2-yl)purine
2-chloro-6-(5-chlorothiophen-2-ylmethylamino)-9-(tetrahydrofuran-2-yl)purine
2-chloro-6-(5-bromothiophen-2-ylmethylamino)-9-(tetrahydrofuran-2-yl)purine
2-chloro-6-(1-thiophen-2-ylethylamino)-9-(tetrahydrofuran-2-yl)purine
2-chloro-6-(cyclopentylmethylamino)-9-(tetrahydrofuran-2-yl)purine More preferably, the compounds of general formula I are selected from the group consisting of:
6-(tetrahydrofuran-2-ylmethylamino)-9-(tetrahydrofuran-2-yl)purine
6-(thiophen-2-ylmethylamino)-9-(tetrahydrofuran-2-yl)purine
2-chloro-6-furfurylamino-9-(tetrahydrofuran-2-yl)purine
2-chloro-6-(tetrahydrofuran-2-ylmethylamino)-9-(tetrahydrofuran-2-yl)purine
2-chloro-6-(thiophen-2-ylmethylamino)-9-(tetrahydrofuran-2-yl)purine.

The invention further encompasses the use of adenine derivatives of general formula I as UV-photoprotective agents in cosmetic compositions, preparations for plant protection and/or in preparations for tissue culture application. Preferred use of the compounds of the invention is the use as agents having a combined anti-senescent and UV-photoprotective effect.

The compounds of the invention show combined anti-senescent and UV-photoprotective effects. Their UV-photoprotective effect was observed against UVA as well as against UVB radiation. They are suitable as components of cosmetic preparations, preparations for plant protection, preparations for tissue culture application. Cosmetic preparations comprising the compounds of the present invention are suitable for the treatment of skin, fur and hair of mammals. The preparations for tissue culture application are suitable for the treatment of plant and mammal cell cultures, wherein the cells are e.g. keratinocytes or fibroblasts.

Object of the invention are further cosmetic preparations, preparations for plant protection, preparations for tissue culture applications, containing compounds according to general formula I. The preparations for tissue culture can be utilized in biotechnologies, especially in tissue cultures for plant micropropagation.

The compounds of the present invention further show immunosuppressive activity through downregulation of tyrosine-protein kinase JAK3 and innate-immunity-related tyrosine-protein kinase HCK and toll-like receptor TLR2. The immunosuppressive activity may be exploited in the cosmetic use of the present compounds for preventing hypersensitive skin reactions, or in medical preparations for treatment of hypersensitive immune response or transplant rejection.

Preparations (Compositions)

Suitable administration for cosmetic application is local, topical. The cosmetic composition typically contains from 0.1 to 95 wt. % of the active ingredient, whereas single-dose forms contain preferably 10 to 90 wt. % of the active ingredient and administration forms which are not single-dose preferably comprise 1 wt. % to 10 wt. % of the active ingredient. The application forms include, e.g., ointments, creams, pastes, foams, tinctures, lipsticks, drops, sprays, dispersions and the like. The compositions are prepared in a known manner, for example by means of conventional mixing, dissolving or lyophilizing processes.

Solutions of the active ingredients, suspensions or dispersions, especially isotonic aqueous solutions, dispersions and suspensions, can be prepared before use, for example in the case of lyophilised compositions which comprise the active substance alone or together with a carrier, for example mannitol.

Suspensions in oil comprise, as the oily component, vegetable, synthetic or semi-synthetic oils. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, erucic acid, brasidic acid or linoleic acid, if appropriate with the addition of antioxidants, for example vitamin E, (3-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and composed of glycerides and polyethylene glycol esters; from Gattefoseé, Paris), "Labrasol" (saturated polyglycolated glycerides prepared by an alcoholysis of TCM and composed of glycerides and polyethylene glycol esters; from Gattefoseé, Paris) and/or "Miglyol 812" (triglyceride of saturated fatty acids of chain length $C_8$ to $C_{12}$ from Hills AG, Germany), and in particular vegetable oils, such as cottonseed oil, almond oil, olive oil, castor oil, sesame oil, soybean oil and, in particular, groundnut oil.

Ointments are oil-in-water emulsions which comprise not more than 70%, preferably 20 to 50% of water or aqueous phase. The fatty phase consists, in particular, of hydrocarbons, for example vaseline, paraffin oil or hard paraffins, which preferably comprise suitable hydroxy compounds, such as fatty alcohols or esters thereof, for example cetyl alcohol, or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are non-aqueous and are in particular hydrocarbon-based, e.g. paraffin, vaseline or paraffin oil, and natural or semi-synthetic lipids, such as hydrogenated coconut fatty acid triglycerides or hydrogenated oils, such as hydrogenated castor or groundnut oil, and partially fatty acid glycerol esters, e.g. glycerol mono- and distearate. They further contain, e.g., fatty alcohols, emulsifiers and additives mentioned above in connection with ointments which increase water binding.

Creams are oil-in-water emulsions containing more than 50% of water. The oil bases used include fatty alcohols, e.g., isopropyl myristate, lanolin, bees wax or hydrocarbons, preferably vaseline (petrolatum) and paraffine oil. Emulsifiers are surface active compounds with predominantly hydrophilic characteristics, such as corresponding non-ionic emulsifiers, e.g., fatty acid polyalcohol esters or ethyleneoxy adducts thereof, e.g., polyglyceridic fatty acids or polyethylene sorbitan esters or acidic polyflyceridic fatty acid esters (Tween), polyoxyethylene fatty acid ethers or polyoxyethylene fatty acid esters; or corresponding ionic emulsifiers, such as alkali sulfate salts of fatty alcohols, such as sodium laurylsulfate, sodium cetylsulfate, or sodium stearylsulfate, which are typically used in the presence of fatty alcohols, e.g., cetyl stearyl alcohol or stearyl alcohol. The aqueous phase additives include agents preventing drying out of the creams, e.g., polyalcohols such as glycerol, sorbitol, propylene glycol and polyethylene glycol, and preservatives and fragrances. Pastes are creams or ointments containing powdered secretion-absorbing components such as metal oxides, e.g., titanium oxides or zinc oxide, further talc or aluminium silicates for binding humidity or secretion.

Foams are applied from pressurized containers and include liquid oil-in-water emulsions in aerosol form, whereas the propellant gases include halogenated hydrocarbons such as chloro-fluoro-lower alkanes, e.g., dichlorofluoromethane and dichlorotetrafluoroethane, or preferably non-halogenated gaseous hydrocarbons, air, $N_2O$ or carbon dioxide. The oily phases used are the same as for ointments and the additives mentioned for ointments are used.

Tinctures and solutions usually comprise an aqueous-ethanolic base, to which humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The invention is further illustrated by the following examples which should not be construed as further limiting.

EXAMPLES OF CARRYING OUT THE INVENTION

Example 1

Preparation of 6-(tetrahydrofuran-2-ylmethyl-amino)-9-(tetrahydrofuran-2-yl)purine (1)

6-Chloro-9-(tetrahydrofuran-2-yl)purine (1 g; 4.46 mmol), tetrahydrofurfurylamine (554 µl; 5.36 mmol) and triethylamine ($Et_3N$) (3.2 ml; 22.3 mmol) were sequentially dissolved in propanol (50 ml). The mixture was stirred under reflux for 4 hours and then concentrated in vacuo. The residue was dissolved in water and extracted into EtOAC using liquid-liquid continuous extractor (24 h). Organic fraction was dried (Na2SO4) and evaporated in vacuo. The product was obtained after purification via column chromatography using (EtOAc:MeOH:$NH_3$; 34:1:1; v:v) as eluent. Yield: 76%. $^1$H NMR (500 MHz, DMSO-$d_6$), ppm: 1.53-1.64 (m, 1H); 1.69-1.89 (m, 3H); 1.95-2.02 (m, 1H); 2.11-2.23 (m, 1H); 2.30-2.44 (m, 2H); 3.37-3.48 (m, 1H); 3.48-3.53 (m, 1H); 3.53-3.60 (m, 1H); 3.70-3.76 (m, 1H); 3.81-3.90 (m, 1H); 3.98 (q, J=7.03 Hz, 1H); 4.09 (q, J=7.44 Hz, 1H); 6.21 (dd, J=6.88, 3.82 Hz, 1H); 7.63 (br. s., 1H); 8.17 (br. s., 1H); 8.21 (s, 1H).

TABLE 1

Compounds prepared according to example 1

| N. | $R_6$ | $R_2$ | Elemental analysis calculated/found % C | % H | % N | ES MS $[M + H]^+$ |
|---|---|---|---|---|---|---|
| 1 | tetrahydrofuran-2-ylmethyl | H | 58.1/58.0 | 6.6/6.6 | 24.2/24.3 | 290.3 |
| 2 | 5-methylfuran-2-ylmethyl | H | 60.2/60.1 | 5.7/5.7 | 23.4/23.5 | 300.3 |
| 3 | 5-hydroxymethylfuran-2-ylmethyl | H | 57.1/57.2 | 5.4/5.4 | 22.2/22.5 | 316.3 |
| 4 | 5-formylfuran-2-ylmethyl | H | 57.5/57.6 | 4.8/4.8 | 22.4/22.2 | 314.3 |
| 5 | 1-furan-2-ylethyl | H | 60.2/60.1 | 5.7/5.8 | 23.4/23.5 | 300.3 |
| 6 | 5-methyltetrahydrofuran-2-ylmethyl | H | 59.4/59.3 | 7.0/7.0 | 23.1/23.2 | 304.4 |
| 7 | 1-tetrahydrofuran-2-ylethyl | H | 59.4/59.2 | 7.0/7.1 | 23.1/23.2 | 304.4 |
| 8 | cyklopentylmethyl | H | 62.7/62.9 | 7.4/7.5 | 24.4/24.5 | 288.4 |

Example 2: Preparation of 6-(thiophen-2-ylmethyl-amino)-9-(tetrahydrofuran-2-yl)purine (9)

6-Chloro-9-(tetrahydrofuran-2-yl)purine (0.5 g; 2.23 mmol), 2-thiophenemethylamine (275 μl; 2.68 mmol) and triethylamine (Et$_3$N) (1.6 ml; 11.15 mmol) were sequentially dissolved in propanol (25 ml) The mixture was stirred under reflux for 3 hours then 2-thiophenemethylamine (23 μl; 0.23 mmol) was added and reaction mixture was stirred under reflux for an additional 1.5 hours. The mixture was concentrated in vacuo. The residue was dissolved in water and extracted into EtOAc. Organic fraction was dried (Na$_2$SO$_4$) and evaporated in vacuo. Product was obtained after precipitation in diethylether. Yield: 61%. $^1$H NMR (500 MHz, DMSO-d$_6$) δ ppm 1.92-2.00 (m, 1H); 2.12-2.22 (m, 1H); 2.31-2.38 (m, 1H); 2.38-2.43 (m, 1H); 3.85 (td, J=7.68, 6.34 Hz, 1H); 4.08 (td, J=7.68, 6.50 Hz, 1H); 4.79 (br. s., 2H); 6.21 (dd, J=6.88, 3.82 Hz, 1H); 6.88 (dd, J=5.04, 3.44 Hz, 1H); 6.97 (dd, J=3.40, 1.03 Hz, 1H); 7.27 (dd, J=5.12, 1.22 Hz, 1H); 8.23 (s, 2H); 8.36 (br. s., 1H).

TABLE 2

Compounds prepared according to example 2

| N. | $R_6$ | $R_2$ | Elemental analysis calculated/found % C | % H | % N | ES MS $[M + H]^+$ |
|---|---|---|---|---|---|---|
| 9 | thiophen-2-ylmethyl | H | 55.8/55.6 | 5.0/5.4 | 23.2/23.3 | 302.4 |
| 10 | 3-methylthiophen-2-ylmethyl | H | 57.1/57.2 | 5.4/5.5 | 22.2/22.3 | 316.4 |
| 11 | 5-methylthiophen-2-ylmethyl | H | 57.1/57.0 | 5.4/5.3 | 22.2/22.1 | 316.4 |
| 12 | 5-chlorothiophen-2-ylmethyl | H | 50.0/50.1 | 4.2/4.3 | 20.9/20.8 | 336.8 |
| 13 | 5-bromothiophen-2-ylmethyl | H | 44.2/44.1 | 3.7/3.8 | 18.4/18.5 | 381.3 |
| 14 | 1-thiophen-2-ylethyl | H | 57.1/57.0 | 5.4/5.5 | 22.2/22.0 | 316.4 |

Example 3: Preparation of 2-chloro-6-furfurylamino-9-(tetrahydrofuran-2-yl)purine (15)

2,6-Dichloro-9-(tetrahydrofuran-2-yl)purine (0.5 g; 1.93 mmol), furfurylamine (204 μl; 2.31 mmol) and triethylamine (Et$_3$N) (1.32 ml; 9.65 mmol) were sequentially dissolved in propanol (25 ml). The mixture was stirred under reflux for 5 hours and then concentrated in vacuo. If product did not cristallize from reaction mixture it was evaporated in vacuo. Crude reaction mixture was precipitated from (CHCl$_3$:EtOH; 1:8; v:v) or (CHCl$_3$:Ether; 1:7; v:v) and filtrated. Solid product was washed with cold water and recrystallized from EtOH

TABLE 3

Compounds prepared according to example 3

| N. | $R_6$ | $R_2$ | Elemental analysis calculated/found % C | % H | % N | ES MS $[M + H]^+$ |
|---|---|---|---|---|---|---|
| 15 | furfuryl | Cl | 52.6/52.5 | 4.4/4.3 | 21.9/21.7 | 320.7 |
| 16 | 5-methylfuran-2-ylmethyl | Cl | 54.0/54.1 | 4.8/4.7 | 21.0/20.9 | 334.8 |
| 17 | 5-hydroxymethylfuran-2-ylmethyl | Cl | 51.5/51.6 | 4.6/4.7 | 20.0/20.1 | 350.8 |

TABLE 3-continued

Compounds prepared according to example 3

| N. | $R_6$ | $R_2$ | Elemental analysis calculated/found | | | ES MS |
|---|---|---|---|---|---|---|
| | | | % C | % H | % N | $[M + H]^+$ |
| 18 | 5-formylfuran-2-ylmethyl | Cl | 51.8/51.9 | 4.1/4.2 | 20.1/20.3 | 348.8 |
| 19 | 1-furan-2-ylethyl | Cl | 54.0/54.1 | 4.8/4.9 | 21.0/21.3 | 334.8 |
| 20 | tetrahydrofuran-2-ylmethyl | Cl | 51.9/51.8 | 5.6/5.7 | 21.6/21.5 | 323.8 |
| 21 | 5-methyltetrahydrofuran-2-ylmethyl | Cl | 53.3/53.4 | 6.0/6.0 | 20.7/20.5 | 338.8 |
| 22 | 1-tetrahydrofuran-2-ylethyl | Cl | 53.3/53.4 | 6.0/6.1 | 20.7/20.6 | 338.8 |
| 23 | thiophen-2-ylmethyl | Cl | 50.1/50.1 | 4.2/4.3 | 20.9/20.8 | 336.8 |
| 24 | 3-methylthiophen-2-ylmethyl | Cl | 51.5/51.6 | 4.6/4.7 | 20.0/20.2 | 350.8 |
| 25 | 5-methylthiophen-2-ylmethyl | Cl | 51.5/51.6 | 4.6/4.7 | 20.0/20.1 | 350.8 |
| 26 | 5-chlorthiophen-2-ylmethyl | Cl | 45.4/45.6 | 3.5/3.7 | 18.9/18.8 | 371.3 |
| 27 | 5-bromthiophen-2-ylmethyl | Cl | 40.6/40.5 | 3.2/3.1 | 16.9/16.8 | 415.7 |
| 28 | 1-thiophen-2-ylethyl | Cl | 51.5/51.6 | 4.6/4.7 | 20.0/20.1 | 350.8 |
| 29 | cyklopentylmethyl | Cl | 56.0/56.1 | 6.3/6.4 | 21.8/21.9 | 322.8 |

Example 4: Evaluation of Cytotoxicity of Novel Derivatives for Skin Cell by MTT In Vitro Test MTT assay is a standard test of toxicity based on photometric measurement of the ability of metabolically active cells to reduce MTT (3-(4,5-dimethylthiazol-2-yl)-2,5-diphenyltetrazolium bromide). Using the assay, the effects of 72 hour treatments with several concentrations of the compounds (sixfold dilution, maximal concentration=50 microM) on viability of skin fibroblasts BJ and keratinocytes HaCaT were evaluated. About 5,000 cells were seeded per well of a 96-well plate 24 hours before the treatment. DMSO vehiculum was used as a negative control. After 72 hour treatment, new medium with MTT (Sigma, M2128) was added to a final concentration of 0.5 mg/ml. After 3 hours, medium was removed and resulting formazan in the cells was dissolved in DMSO. The absorbance was measured at 570 nm (640 nm reference wavelength). The IC50 values were calculated from the dose-response curves. 6-furfurylaminopurine riboside was used as positive controls. The following results were obtained.

TABLE 4

Cytotoxicity of prepared compounds in MTT in vitro assay.

| Compound | $IC_{50}$ (µM) |
|---|---|
| dimethylsulfoxid | >100 |
| 6-(tetrahydrofuran-2-ylmethylamino)-9-(tetrahydrofuran-2-yl)purine | >100 |
| 6-(thiophen-2-ylmethylamino)-9-(tetrahydrofuran-2-yl)aminopurine | >100 |
| 2-chloro-6-furfurylamino-9-(tetrahydrofuran-2-yl)purine | >100 |
| 6-furfurylamino-9-ribosylpurine (comperative example) | ≤3 |

Example 5: Anti-Senescent Activity of Novel Compounds Tested in Senescent Bioassay on Wheat Leaf Segments Seeds of winter wheat, *Triticum aestivum* cv. Hereward, were washed under running water for 24 hours and then sown on vermiculite soaked with Knop's solution. They were placed in the growth chamber at 25° C. with a 16/8 h light period at 50 µm$^2$·s$^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 µL of the tested derivative solution each. The entire plate was inserted into a plastic box lined with paper tissues soaked in distilled water to prevent leaf sections from drying out. After 96 h incubation in the dark at 25° C., the leaves were removed and chlorophyll extracted by heating at 80° C. for 10 min in 5 mL of 80% ethanol (v/v). The sample volume was then restored to 5 mL by the addition of 80% ethanol (v/v). The absorbance of the extract was recorded at 665 nm. In addition, chlorophyll extracts from fresh leaves and leaf tips incubated in deionised water were measured. The results are means of five replicates and the entire test was repeated twice. In each experiment activities of the novel compounds were tested and compared with activity of BAP, which is known to be highly active cytokinin.

The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used. The activity obtained for $10^{-4}$ M of BAP was postulated as 100%. Kinetin was used as the second standard. Newly prepared compounds generally exceeded the efficiency of standard (BAP) by 10% of its activity (Tab. 5).

TABLE 5

Relative biological activity in detached wheat leaf senescence (chlorophyll retention) biotest compared with activity of 6-benzylaminopurine (BAP) standard (100% means activity of BAP in concentration $10^{-4}$ mol · l$^{-1}$)

| Compound | maximum effective concentration (mol · l$^{-1}$) | activity (%) [$10^{-4}$ mol · l$^{-1}$ BAP = 100%] |
|---|---|---|
| BAP (comperative example) | $10^{-4}$ | 100 ± 1 |
| kinetin (comperative example) | $10^{-4}$ | 98 ± 4 |
| 6-furfurylamino-9-(tetrahydrofuran-2-yl)purin | $10^{-4}$ | 114 ± 3 |

TABLE 5-continued

Relative biological activity in detached wheat leaf senescence (chlorophyll retention) biotest compared with activity of 6-benzylaminopurine (BAP) standard (100% means activity of BAP in concentration $10^{-4}$ mol·$l^{-1}$)

| Compound | maximum effective concentration (mol·$l^{-1}$) | activity (%) [$10^{-4}$ mol·$l^{-1}$ BAP = 100%] |
|---|---|---|
| 6-(3-methylthiophen-2-ylmethyl-amino)-9-(tetrahydrofuran-2-yl)purine | $10^{-4}$ | 110 ± 7 |
| 6-(tetrahydrofuran-2-ylmethyl-amino)-9-(tetrahydrofuran-2-yl)purine | $10^{-4}$ | 125 ± 9 |
| 6-(thiophen-2-ylmethylamino)-9-(tetra-hydrofuran-2-yl)purine | $10^{-4}$ | 112 ± 5 |
| 2-chloro-6-(tetrahydrofuran-2-yl-methylamino)-9-(tetrahydro-furan-2-yl)purine | $10^{-4}$ | 127 ± 5 |

Example 6: In Vitro Cytotoxic Activity of New Derivatives on Cancer Cell Lines One of the parameters used as the base for cytotoxic analysis is metabolic activity of viable cells. Microtiter assay, which uses the Calcein AM, is now widely used to quantify cell proliferation and cytotoxicity. The quantity of reduced Calcein AM corresponds to the number of viable cells in culture. The cell lines of breast cancer (MCF-7), human erythromleukemia (K562), BJ human fibroblast cells (BJ) and human keratinocyte cell line (HaCaT) were used for routine screening of cytotoxicity of the compounds. The cells were maintained in Nunc/Corning 80 $cm^2$ plastic bottles and grown in media for cell culture (DMEM containing 5 g/l of glucose, 2 mM of glutamin, 100 U/ml of penicilin, 100 μg/ml of streptomycin, 10% of fetal bovine serum and sodium hydrogencarbonate). Cell suspensions were diluted according to cell types and according to expected final cell density ($10^4$ of cells per well according to characteristics of cell growth), pippeted 80 μl of cell suspension on 96-well microtiter plates. Innoculates were stabilized by 24 hrs preincubation at 37° C. in $CO_2$. Particular concentrations of tested compounds were added in time zero as 20 μl aliquotto wells of microtiter plates. Usually, the compounds were diluted into six concentrations in four-fold dilution series. In routine testing, the highest well concentration was 166.7 μM, of change dependent on the substance. All drug concentrations were examined in duplicates. The incubation of cells with tested derivatives lasted 72 hrs at 37° C., 100% humidity and in the atmosphere of $CO_2$. At the end of the incubation period, the cells were tested and analysed according to the addition of Calcein AM (Molecular probes) solution and the incubation lasted for next 1 hour. Fluorescence (FD) was measured using Labsystem FIA reader Fluorskan Ascent (Microsystems). The survival of tumor cells (The tumor cell survival-TCS) was counted according to equation: $GI_{50}=(FD_{well\ with\ derivative}/FD_{control\ well})\times 100\%$. The value of $GI_{50}$, that is equal to the concentration of compound at which 50% of tumour cells are terminated. To evaluate the antitumor activity was tested toxicity of new derivatives on panel of cell lines of different histogenetic and species origin (Tab. 6, G150 concentration given in μM). It turned out that new compounds showed to be non toxic for neither of all tested tumor lines nor for nonmalignant cell lines BJ and HaCaT. Effective derivatives killed tumor cells in concentrations close to 0.1 to 50. None of the newly prepared compounds only reached the value.

TABLE 6

Cytotoxicity of newly prepared compouds for various cell lines

| Compound | MCF-7 | K562 | BJ | HaCaT |
|---|---|---|---|---|
| 6-furfurylamino-9-(tetrahydrofuran-2-yl)purine | >100 | >100 | >100 | >100 |
| 6-(tetrahydrofuran-2-ylmethylamino)-9-(tetrahydrofuran-2-yl)purine | >100 | >100 | >100 | >100 |
| 6-(thiophen-2-ylmethylamino)-9-(tetrahydrofuran-2-yl)purine | >100 | >100 | >100 | >100 |
| 2-chloro-6-(tetrahydrofuran-2-ylmethylamino)-9-(tetrahydrofuran-2-yl)purine | >100 | >100 | >100 | >100 |

Example 7: In Vitro Test of Phototoxic Effects of Test Compounds on Normal Human Dermal Fibroblasts Phototoxic potential of test compound was determined by modified in vitro test validated phototoxicity evaluation (Spielmann H, Balls M, Dupuis J, Pape W J, Pechovitch G, de Silva O, Holzhiitter H G, Clothier R, Desolle P, Gerberick F, Liebsch M, Lovell W W, Maurer T, Pfannenbecker U, Potthast J M, Csato M, Sladowski D, Steiling W, Brantom P. The International EU/COLIPA In Vitro Phototoxicity Validation Study: Results of Phase II (Blind Trial). Part 1: The 3T3 NRU Phototoxicity Test. Toxicol In Vitro. 1998; 12:305-27). Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. Fibroblasts were used between the 2nd and 4th passage. For all experiments the fibroblasts were seeded onto 96-well plates at a density of $0.8\times 10^5$ cells/ml (0.2 ml per well) of cultivation medium (DMEM supplemented with fetal calf serum (10%, v/v), penicillin (100 mg/ml) and streptomycin (100 U/ml)). Test substances included compounds number 1, 3, 9, 15 and 20. Compounds were dissolved in DMSO and then diluted in serum free medium (DMEM supplemented with penicillin (100 mg/ml) and streptomycin (100 U/ml)). After 24 h incubation was cultivation medium changed to serum free medium containing test compound or DMSO (negative control). The final applied concentrations range 3.9-125 μmol/l. As a control, serum free medium supplemented with appropriate concentration of DMSO (0.5%, v/v) was used. In parallel with test compound, chlorpromazine (CPZ; 0.8-50 μmol/l) was used as a known phototoxic compound. The test compound was in parallel applied on two 96-well plates with NHDF. After 60 minutes incubation with test compound medium was discarded, cells were washed two-times with PBS and PBS supplemented with glucose (1 mg/ml) was applied. A plate was then exposed to a non-cytotoxic dose of UVA radiation (5.0 $J/cm^2$) using a solar simulator SOL 500 (Dr. Hoenle Technology, Germany) equipped with a H1 filter transmitting wavelengths of 320-400 nm. Intensity of UVA radiation was evaluated before each irradiation by UVA-meter. A control (non-irradiated) plate was for the period of irradiation incubated in dark. After UVA exposure PBS with glucose was discarded and serum free medium was applied.

After 24 hours (37° C., 5% $CO_2$) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and $CaCl_2$ (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetitions with use of cells from four donors to minimize individual sensitivity of donor cells. Phototoxic effect was evaluated as % of viability of control cells that was calculated from experimental data (absorbance) according to the following equation:

$$\text{Viability (\% of control)} = \left(\frac{(A_S - A_B)}{(A_C - A_B)}\right) \cdot 100$$

$A_S$ . . . absorbance of sample (cells pre-incubated with test compound in serum free medium and irradiated)
$A_C$ . . . absorbance of control (cells pre-incubated with DMSO in serum free medium and irradiated)
$A_B$ . . . absorbance of background (extraction solution)

Result: Treatment with test compounds and following exposure to non-toxic UVA dose did not cause decrease in cell viability—incorporation of NR and thus test compound can be considered as non-phototoxic in the used concentration range (3.9-125 µmol/l). Results are given in Tab. 7. A well-known phototoxic compound chlorpromazine, which can be used for comparison, decreases the viability of NHDF cells: on exposure to UVA radiation (UVA+), the viability decreases below 80% of control in the presence of 6.3 µmol/l of chlorpromazine, while the viability of unirradiated cells (UVA−) decreases below 80% in the presence of 25 µmol/l of chlorpromazine. A Above data indicate that test compounds are safe for cosmetic and dermatological application including use with following exposure of treated skin with solar radiation.

TABLE 7

UVA-induced effects of test compounds on NHDF viability.

| | | 3.9 | 7.8 | 15.6 | 31.3 | 62.5 | 125 |
|---|---|---|---|---|---|---|---|
| 1 (µmol/l) | | | | | | | |
| −UVA | % control | 96.6 | 106.5 | 99.6 | 102.4 | 102.3 | 109.7 |
| | SMODCH | 7.4 | 9.2 | 3.7 | 2.1 | 5.8 | 10.5 |
| +UVA | % control | 105.1 | 110.6 | 106.8 | 109.5 | 103.3 | 107.5 |
| | SMODCH | 10.3 | 10.7 | 13.4 | 10 | 8.9 | 8.9 |
| 3 (µmol/l) | | | | | | | |
| −UVA | % control | 103 | 104.9 | 104.2 | 107.7 | 106.6 | 110.4 |
| | SMODCH | 4.2 | 5.4 | 5 | 8 | 3.2 | 4 |
| +UVA | % control | 101.04 | 106.46 | 102.28 | 107.4 | 110.49 | 111.8 |
| | SMODCH | 1.9 | 7.8 | 2.9 | 8.2 | 8.3 | 7.1 |
| 9 (µmol/l) | | | | | | | |
| −UVA | % control | 100 | 103 | 100.5 | 106.7 | 107.9 | 108.4 |
| | SMODCH | 0.8 | 3.4 | 2 | 0.3 | 3.2 | 0.2 |
| +UVA | % control | 97.8 | 102.3 | 100.8 | 105.9 | 102.8 | 106.3 |
| | SMODCH | 1.5 | 4.4 | 1.4 | 4.3 | 3.7 | 1.2 |
| 15 (µmol/l) | | | | | | | |
| −UVA | % control | 100.3 | 103.5 | 104.3 | 105.4 | 106.3 | 101.2 |
| | SMODCH | 1.6 | 4.3 | 3.2 | 4.7 | 3.9 | 1.8 |
| +UVA | % control | 100.1 | 101.5 | 102.6 | 102.9 | 103.3 | 97.3 |
| | SMODCH | 0.2 | 2.1 | 0.8 | 2.7 | 2.1 | 4 |
| 20 (µmol/l) | | | | | | | |
| −UVA | % control | 103.1 | 102.9 | 100.6 | 105.6 | 102 | 104 |
| | SMODCH | 1.7 | 5.2 | 1.3 | 5.4 | 1.1 | 1.8 |
| +UVA | % control | 100.1 | 102.9 | 100.4 | 102.7 | 105.1 | 104.8 |
| | SMODCH | 3.5 | 4 | 3.7 | 3.9 | 6.1 | 5.2 |

Example 8: In Vitro Test of Photoprotective Effects of 6-(tetrahydrofuran-2-ylmethylamino)-9-(tetrahydrofuran-2-yl)purine on Dermal Fibroblasts Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. Fibroblasts were used between the 2nd and 4th passage. For all experiments the fibroblasts were seeded onto 96-well plates at a density of $0.8 \times 10^5$ cells/ml (0.2 ml per well) of cultivation medium (DMEM supplemented with foetal calf serum (10%, v/v), penicillin (100 mg/ml) and streptomycin (100 U/ml)). Test compounds included 6-(tetrahydrofuran-2-ylmethylamino)-9-(tetrahydrofuran-2-yl)purine (1). Compounds were dissolved in DMSO and then diluted in serum free medium (DMEM supplemented with penicillin (100 mg/ml) and streptomycin (100 U/ml)). After 24 h incubation was cultivation medium changed to serum free medium containing test compound or DMSO (negative control). The final applied concentrations range of 6-(tetrahydrofuran-2-ylmethylamino)-9-(tetrahydrofuran-2-yl)purine was 3.9-500 µmol/ll. As a control serum free medium supplemented with appropriate concentration of DMSO (0.5%, v/v) was used. Each test compound was in parallel applied on two 96-well plates with NHDF. After 60 minutes incubation medium with test compound was discarded, cells were washed two-times with PBS and PBS supplemented with glucose (1 mg/ml) was applied. To study UVA photoprotection, a plate was exposed to a cytotoxic dose of UVA radiation (7.5 $J/cm^2$) using a solar simulator SOL 500 (Dr. Hoenle Technology, Germany) equipped with a H1 filter transmitting wavelengths of 320-400 nm. To study UVB photoprotection, a plate was exposed to a cytotoxic dose of UVB radiation (400 $mJ/cm^2$) using the solar simulator equipped with a H2 filter transmitting wavelengths of 295-320 nm. Intensity of UVA or UVB radiation was evaluated before each irradiation by UVA- or UVB-meter. Control (non-irradiated) plates were for the period of irradiation incubated in dark. After UVA or UVB exposure PBS with glucose was discarded and serum free medium was applied. After 24 hours (37° C., 5% $CO_2$) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and $CaCl_2$ (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetitions with use of cells from four donors to minimize individual sensitivity of donor cells. Photoprotective effect was evaluated by comparison of experimental data (absorbance) of test compounds with a positive control and a negative control (according to the following equation:

$$\text{Protection (\%)} = 100 - \left|\frac{As - Anc}{Apc - Anc}\right| \cdot 100$$

As . . . absorbance of sample (cells pre-incubated with test compounds in serum free medium and irradiated)
Anc . . . absorbance of negative control (cells pre-incubated with s DMSO in serum free medium and non-irradiated=incubated in dark)
Apc . . . absorbance of positive control (cells pre-incubated with s DMSO in serum free medium and irradiated)

Results: Cells pre-incubated with test compound and exposed to UVA or UVB radiation showed higher viability (ability to incorporate NR) compared to those pre-incubated with DMSO (control) and UVA or UVB irradiated (Tab. 8 and 9).

TABLE 8

Photoprotective effect of 6-(tetrahydrofuran-2-ylmethylamino)-9-(tetrahydrofuran-2-yl)purine (1) on UVA-induced damage to NHDF. UVA photoprotection

| Concentration (µmol/l) | 1 protection (%) |
| --- | --- |
| 3.9 | 27.7 ± (6.9) |
| 7.8 | 57.4 ± (14.4) |
| 15.6 | 43.2 ± (10.8) |
| 31.3 | 47.5 ± (11.9) |
| 62.5 | 41.3 ± (10.3) |
| 125 | 49 ± (12.3) |
| 250 | 45.3 ± (11.3) |
| 500 | 18.5 ± (4.6) |

TABLE 9

Photoprotective effect of 6-(tetrahydrofuran-2-ylmethylamino)-9-(tetrahydrofuran-2-yl)purine (1) on UVB-induced damage to NHDF. UVB photoprotection

| Concentration (µmol/l) | 1 protection (%) |
| --- | --- |
| 3.9 | 4.9 ± (1.2) |
| 7.8 | 44.1 ± (11) |
| 15.6 | 35 ± (8.7) |
| 31.3 | 38.3 ± (9.6) |
| 62.5 | 44.4 ± (11.1) |
| 125 | 42.7 ± (10.7) |
| 250 | 46.6 ± (11.6) |
| 500 | 26.3 ± (6.6) |

Example 9: In Vitro Test of Photoprotective Effects of Test Compounds on Dermal Fibroblasts Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. Fibroblasts were used between the 2nd and 4th passage. For all experiments the fibroblasts were seeded onto 96-well plates at a density of $0.8 \times 10^5$ cells/ml (0.2 ml per well) of cultivation medium (DMEM supplemented with fetal calf serum (10%, v/v), penicillin (100 mg/ml) and streptomycin (100 U/ml)). Test substances included compounds number 1, 3, 9, 15 and 20. Compounds were dissolved in DMSO and then diluted in serum free medium (DMEM supplemented with penicillin (100 mg/ml) and streptomycin (100 U/ml)). After 24 h incubation was cultivation medium changed to serum free medium containing test compound or DMSO (negative control). The final applied concentrations range was 3.9-31.3 µmol/ll. As a control serum free medium supplemented with appropriate concentration of DMSO (0.5%, v/v) was used. Rosmarinic acid was used as positive control. Each test compound was in parallel applied on two 96-well plates with NHDF. After 60 minutes incubation medium with test compound was discarded, cells were washed two-times with PBS and PBS supplemented with glucose (1 mg/ml) was applied. To study UVA photoprotection, a plate was exposed to a cytotoxic dose of UVA radiation (7.5 J/cm$^2$) using a solar simulator SOL 500 (Dr. Hoenle Technology, Germany) equipped with a H1 filter transmitting wavelengths of 320-400 nm. To study UVB photoprotection, a plate was exposed to a cytotoxic dose of UVB radiation (150 mJ/cm$^2$) using the solar simulator equipped with a H2 filter transmitting wavelengths of 295-320 nm. Intensity of UVA or UVB radiation was evaluated before each irradiation by UVA- or UVB-meter. Control (non-irradiated) plates were for the period of irradiation incubated in dark. After UVA or UVB exposure PBS with glucose was discarded and serum free medium was applied. After 24 hours (37° C., 5% CO$_2$) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl$_2$ (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetitions with use of cells from four donors to minimize individual sensitivity of donor cells. Photoprotective effect was evaluated by comparison of experimental data (absorbance) of test compounds with a positive control and a negative control (according to the following equation:

$$\text{Protection (\%)} = 100 - \left|\frac{As - Anc}{Apc - Anc}\right| \cdot 100$$

As . . . absorbance of sample (cells pre-incubated with test compounds in serum free medium and irradiated)
Anc . . . absorbance of negative control (cells pre-incubated with s DMSO in serum free medium and non-irradiated=incubated in dark)
Apc . . . absorbance of positive control (cells pre-incubated with s DMSO in serum free medium and irradiated)

Results: Cells pre-incubated with test compounds and exposed to UVA or UVB radiation showed higher viability (ability to incorporate NR) compared to those pre-incubated with DMSO (control) and UVA or UVB irradiated (Tab. 10 and 11). All test compounds showed higher or comparable photoprotective activity with rosmarinic acid used as positive control. Therefore test compounds has high photoprotective potential.

TABLE 10

Photoprotective effect of test compounds and rosmarinic acid (RA, positive control) on UVA-induced damage to NHDF.

|  | 3.9 | 7.8 | 15.6 | 31.3 |
|---|---|---|---|---|
| 3 (µmol/l) | | | | |
| Protection (%) | 14.7 | 16.3 | 24.6 | 25.8 |
| SMODCH | 3.2 | 3.3 | 5.8 | 4.5 |
| 9 (µmol/l) | | | | |
| Protection (%) | 41.3 | 44.4 | 45.7 | 52.0 |
| SMODCH | 18.0 | 12.6 | 9.5 | 10.8 |
| 15 (µmol/l) | | | | |
| Protection (%) | 24.5 | 29.9 | 33.0 | 35.3 |
| SMODCH | 11.9 | 10.8 | 12.1 | 11.5 |
| 20 (µmol/l) | | | | |
| Protection (%) | 5.9 | 10.7 | 11.5 | 16.2 |
| SMODCH | 3.2 | 3.5 | 5.4 | 4.1 |
| RA | | | | |
| Protection (%) | 6.1 | 14.7 | 17.0 | 19.3 |
| SMODCH | 3.0 | 3.5 | 3.8 | 3.4 |

TABLE 11

Photoprotective effect of test compounds and rosmarinic acid (RA, positive control) on UVB-induced damage to NHDF.

|  | 3.9 | 7.8 | 15.6 | 31.3 |
|---|---|---|---|---|
| 3 (µmol/l) | | | | |
| Protection (%) | 43.6 | 53.1 | 47.4 | 48.4 |
| SMODCH | 10.7 | 9.1 | 16.9 | 13.9 |
| 9 (µmol/l) | | | | |
| Protection (%) | 34.9 | 62.6 | 64.4 | 68.7 |
| SMODCH | 23.7 | 21.4 | 14.6 | 6.2 |
| 15 (µmol/l) | | | | |
| Protection (%) | 39.9 | 55.2 | 53 | 60.2 |
| SMODCH | 15.1 | 14.2 | 17.1 | 21 |
| 20(µmol/l) | | | | |
| Protection (%) | 39.8 | 58.3 | 58.2 | 60 |
| SMODCH | 18.3 | 19.3 | 23.2 | 18.8 |
| RA | | | | |
| Protection (%) | 36.8 | 50.9 | 52.9 | 67.7 |
| SMODCH | 5.9 | 5.8 | 11.8 | 5.1 |

Example 10: In Vitro Test of Phototoxic Effects of 6-(tetrahydrofuran-2-ylmethylamino)-9-(tetrahydrofuran-2-yl)purine on Normal Human Epidermal Keratinocytes Normal Human Epidermal Keratinocytes (NHEK) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. NHEK were used between the 3rd and 4th passage. For all experiments the keratinocytes were seeded onto 96-well plates at a density of 1×104 cells/ml (0.2 ml per well) of growth medium for keratinocytes (EpiLife®) supplemented with Human Keratinocyte Growth Supplement Kit and antibiotics (penicillin (100 mg/ml), streptomycin (100 mg/ml) and ampicillin (250 µg/ml)). Test compounds included 6-(tetrahydrofuran-2-ylmethylamino)-9-(tetrahydrofuran-2-yl)purine (1). Compound was dissolved in DMSO and then diluted in serum free medium (EpiLife® supplemented with penicillin (100 mg/ml) and streptomycin (100 U/ml) and ampicillin (250 µg/ml)). After 24 h incubation was growth medium changed to serum free medium containing test compound or DMSO (negative control). The final applied concentrations range was 3.9-500 µmol/l. As a control, serum free medium supplemented with appropriate concentration of DMSO (0.5%, v/v) was used. In parallel with test compound, chlorpromazine (CPZ; 0.8-50 µmol/l) was used as a known phototoxic compound. The test compound was in parallel applied on two 96-well plates with NHEK. After 60 minutes incubation with test compound medium was discarded, cells were washed two-times with PBS and PBS supplemented with glucose (1 mg/ml) was applied. A plate was then exposed to a non-cytotoxic dose of UVA radiation (5.0 J/cm2) using a solar simulator SOL 500 (Dr. Hoenle Technology, Germany) equipped with a H1 filter transmitting wavelengths of 320-400 nm. Intensity of UVA radiation was evaluated before each irradiation by UVA-meter. A control (non-irradiated) plate was for the period of irradiation incubated in dark.

After UVA exposure PBS with glucose was discarded and serum free medium was applied. After 24 hours (37° C., 5% CO2) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl2 (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetition with use of cells from four donors to minimize individual sensitivity of donor cells. Phototoxic effect was evaluated as % of viability of control cells that was calculated from experimental data (absorbance) according to the following equation:

$$\text{Viability (\% of control)} = \left(\frac{(A_S - A_B)}{(A_C - A_B)}\right) \cdot 100$$

AS . . . absorbance of sample (cells pre-incubated with test compound in serum free medium and irradiated)
AC . . . absorbance of control (cells pre-incubated with DMSO in serum free medium and irradiated)
AB . . . absorbance of background (extraction solution)
Result: Treatment with test compound and following exposure to non-toxic UVA dose did not cause decrease in cell viability—incorporation of NR and thus test compound can be considered as non-phototoxic in the used concentration range (3.9-500 µmol/l). Results are given in Tab. 12. A well-known phototoxic compound chlorpromazine, which can be used for comparison, decreases the viability of NHEK cells: on exposure to UVA radiation (UVA+), the viability decreases below 80% of control in the presence of 0.6 µmol/l of chlorpromazine, while the viability of unirradiated cells (UVA−) decreases below 50% in the presence of 12.5 µmol/l of chlorpromazine. A. Above data indicate that test compounds are safe for cosmetic and dermatological application including use with following exposure of treated skin with solar radiation.

TABLE 12

UVA-induced effects of 6-(tetrahydrofuran-2-ylmethylamino)-9-(tetrahydrofuran-2-yl)purine on NHEK viability

| Concentration | 1 % of control | |
|---|---|---|
| (µmol/l) | −UVA | +UVA |
| 3.9 | 112.2 ± (11) | 109.1 ± (2.3) |
| 7.8 | 135.5 ± (8.2) | 120.6 ± (1.6) |
| 15.6 | 116.5 ± (2.8) | 110 ± (2.9) |
| 31.3 | 119.1 ± (8.7) | 115.1 ± (2.8) |
| 62.5 | 121 ± (8.7) | 105.9 ± (8.7) |
| 125 | 119 ± (2.8) | 111.7 ± (6.8) |
| 250 | 110.8 ± (12.4) | 112.1 ± (3.7) |
| 500 | 105.7 ± (7.1) | 101.2 ± (3.3) |

Example 11: Example 8: In Vitro Test of Photoprotective Effects of 6-(tetrahydrofuran-2-ylmethylamino)-9-(tetrahydrofuran-2-yl)purine on normal human epidermal keratinocytes Normal Human Epidermal Keratinocytes (NHEK) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. NHEK were used between the 3rd and 4th passage. For all experiments the keratinocytes were seeded onto 96-well plates at a density of $1 \times 10^4$ cells/ml (0.2 ml per well) of growth medium for keratinocytes (EpiLife®) supplemented with Human Keratinocyte Growth Supplement Kit and antibiotics (penicillin (100 mg/ml), streptomycin (100 mg/ml) and ampicillin (250 µg/ml)). Test compounds included 6-(tetrahydrofuran-2-ylmethylamino)-9-(tetrahydrofuran-2-yl)purine (1). Compound was dissolved in DMSO and then diluted in serum free medium (EpiLife® supplemented with penicillin (100 mg/ml) and streptomycin (100 U/ml) and ampicillin (250 µg/ml)). After 24 h incubation was growth medium changed to serum free medium containing test compound. The final applied concentration range was 3.9-500 µmol/l. As a control, serum free medium supplemented with appropriate concentration of DMSO (0.5%, v/v) was used. After 60 minutes incubation with test compound medium was discarded, cells were washed two-times with PBS and PBS supplemented with glucose (1 mg/ml) was applied. To study UVA photoprotection, a plate was exposed to a cytotoxic dose of UVA radiation (7.5 J/cm2) using a solar simulator SOL 500 (Dr. Hoenle Technology, Germany) equipped with a H1 filter transmitting wavelengths of 320-400 nm. To study UVB photoprotection, a plate was exposed to a cytotoxic dose of UVB radiation (200 mJ/cm2) using the solar simulator equipped with a H2 filter transmitting wavelengths of 295-320 nm. Intensity of UVA or UVB radiation was evaluated before each irradiation by UVA- or UVB-meter. Control (non-irradiated) plates were for the period of irradiation incubated in dark. After UVA or UVB exposure PBS with glucose was discarded and serum free medium was applied.

After 24 hours (37° C., 5% CO2) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl2 (1%, m/v) in ratio 1:1 and then NR was dissolved in methanol (50%, v/v) with acetic acid (1%, v/v). After 5 minutes of intensive shaking absorbance was measured at 540 nm.

Experiments were performed in four independent repetitions with use of cells from four donors to minimize individual sensitivity of donor cells. Photoprotective effect was evaluated by comparison of experimental data (absorbance) of test compounds with a positive control and a negative control (according to the following equation:

$$\text{Protection (\%)} = 100 - \left| \frac{As - Anc}{Apc - Anc} \right| \cdot 100$$

As . . . absorbance of sample (cells pre-incubated with test compounds in serum free medium and irradiated)

Anc . . . absorbance of negative control (cells pre-incubated with s DMSO in serum free medium and non-irradiated=incubated in dark)

Apc . . . absorbance of positive control (cells pre-incubated with s DMSO in serum free medium and irradiated)

Results: Cells pre-incubated with test compound and exposed to UVA or UVB radiation showed higher viability (ability to incorporate NR) compared to those pre-incubated with DMSO (control) and UVA or UVB irradiated (Tab. 13 and 14). Therefore test compound has high photoprotective potential.

TABLE 13

Photoprotective effect of 6-(tetrahydrofuran-2-ylmethylamino)-9-(tetrahydrofuran-2-yl)purine (1) on UVA-induced damage to NHEK UVA photoprotection

| Concentration (µmol/l) | 1 protection (%) |
|---|---|
| 3.9 | 39.7 ± (12.9) |
| 7.8 | 60.2 ± (16.1) |
| 15.6 | 53.5 ± (12.4) |
| 31.3 | 46.8 ± (11.8) |
| 62.5 | 47.9 ± (8.9) |
| 125 | 51.7 ± (4.8) |
| 250 | 48 ± (3.2) |
| 500 | 30 ± (13.5) |

TABLE 14

Photoprotective effect of 6-(tetrahydrofuran-2-ylmethylamino)-9-(tetrahydrofuran-2-yl)purine (1) on UVb-induced damage to NHEK UVB photoprotection

| Concentration (µmol/l) | 1 % protection (%) |
|---|---|
| 3.9 | 53.5 ± (7.6) |
| 7.8 | 72 ± (6) |
| 15.6 | 69.8 ± (8.6) |
| 31.3 | 65.9 ± (9) |
| 62.5 | 65.9 ± (5) |
| 125 | 72.9 ± (6.9) |
| 250 | 65.7 ± (3.6) |
| 500 | 28 ± (3.2) |

Example 12: The Effect of Compounds on Lifespan of *Caenorhabditis elegans*

*Caenorhabditis elegans* is a model organism used for identification of compounds with possible beneficial effect on human aging and age-related diseases. The list of compounds that prolong the lifespan of *C. elegans* and are known to have beneficial effect on human health includes resveratrol, curcumin and many others. Some substances that prolong the lifespan of worms are also used in skin rejuvenating and anti-aging cosmetics, for example vitamin E, coenzyme Q10, green tea or pomegranade extracts and cytokinin kinetin. The *Caenorhabditis elegans* strain used in this experiment was fem-1/HT17. This strain has a heat-inducible mutation which causes all worms to develop into females when cultivated in 25° C. (13). That prevents further reproduction and contamination of the experiment with progeny. Compounds dissolved in DMSO (100 mM stock solutions) were added into fresh NGM (nematode growth medium) to the final concentration of 10 and 50 or 100 μM and pipetted onto a Petri dish. Medium with DMSO vehiculum alone and non-treated medium were used as negative control. After solidification of NGM, the plates were seeded with 100 μl of 20× concentrated overnight suspension of *Escherichia coli* strain OP50 in LB medium. Bacteria on plates were allowed to grow overnight in 37° C. Age synchronized young adults (obtained by hypochlorite treatment) were then pipetted onto plates. Plates were kept in 25° C. In regular time intervals (1-3 days), the plates were scanned on an Epson perfection V700 photo flatbed scanner. The number of surviving worms was established by image analysis based on comparison of several subsequent photographs and identification of moving objects. Pictures were analyzed in Fiji similarly as described here. Scripts from the original publication were slightly modified and the parameters adjusted to better suit our photo resolution and lighting. Three subsequent pictures of a plate were compared with each other. The average of the 3 resulting numbers was used to reduce the possibility of error. The overall results were then analyzed in programs OASIS and ED50v10. The statistical significance was evaluated by Log-Rank test and P-values were corrected by Bonferroni correction. The results are shown in table 15. Compounds 1, 15 and 20 significantly prolonged the lifespan of worms.

TABLE 15

The effect of compounds on lifespan of *Caenorhabditis elegans* (in days)

|  | DMSO | 15 10 μM | 15 100 μM | 20 10 μM | 20 100 μM | 1 10 μM | 1 100 μM |
|---|---|---|---|---|---|---|---|
| median | 8.7 | 9.4 | 10.3 | 11.2 | 10.2 | 10.3 | 10.2 |
| average | 10.9 | 11.3 | 13.8 | 12.4 | 11.2 | 11.9 | 12.6 |

Example 13: In Vitro Test of Phototoxic Effects of Test Compounds on HaCaT

Spontaneously Immortalized Aneuploid Human Keratinocyte Cell Line (HaCaT) was bought from CLS (Eppeheim, Germany) and used as an in vitro model. For all experiments the keratinocytes were seeded onto 96-well plates at a density of $1.6 \times 10^5$ cells/ml (0.2 ml per well) of growth medium (DMEM supplemented with fetal bovine serum (10%), penicillin (100 mg/ml) and streptomycin (100 U/ml)).

Test substances included compounds number 3, 9, 15 and 20. Compounds were dissolved in DMSO and then diluted in serum free medium (DMEM supplemented penicillin (100 mg/ml) and streptomycin (100 U/ml)). After 24 h incubation was growth medium changed to serum free medium containing test compound or DMSO (negative control). The final applied concentrations range was 3.9-125 μmol/l. As a control, serum free medium supplemented with appropriate concentration of DMSO (0.5%, v/v) was used. In parallel with test compound, chlorpromazine (CPZ; 0.8-50 μmol/l) was used as a known phototoxic compound. The test compound was in parallel applied on two 96-well plates with HaCaT. After 60 minutes incubation with test compound medium was discarded, cells were washed two-times with PBS and PBS supplemented with glucose (1 mg/ml) was applied. A plate was then exposed to a non-cytotoxic dose of UVA radiation (5.0 J/cm2) using a solar simulator SOL 500 (Dr. Hoenle Technology, Germany) equipped with a H1 filter transmitting wavelengths of 320-400 nm. Intensity of UVA radiation was evaluated before each irradiation by UVA-meter. A control (non-irradiated) plate was for the period of irradiation incubated in dark. After UVA exposure PBS with glucose was discarded and serum free medium was applied. After 24 hours (37° C., 5% CO2) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl2 (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetition with use of cells from four donors to minimize individual sensitivity of donor cells. Phototoxic effect was evaluated as % of viability of control cells that was calculated from experimental data (absorbance) according to the following equation:

$$\text{Viability (\% of control)} = \left(\frac{(A_S - A_B)}{(A_C - A_B)}\right) \cdot 100$$

AS . . . absorbance of sample (cells pre-incubated with test compound in serum free medium and irradiated)
AC . . . absorbance of control (cells pre-incubated with DMSO in serum free medium and irradiated)
AB . . . absorbance of background (extraction solution)

Result: Treatment with test compounds and following exposure to non-toxic UVA dose did not cause decrease in cell viability—incorporation of NR and thus test compound can be considered as non-phototoxic in the used concentration range (3.9-125 μmol/l). Results are given in Tab. 16. A well-known phototoxic compound chlorpromazine, which can be used for comparison, decreases the viability of HaCaT cells: on exposure to UVA radiation (UVA+), the viability decreases below 80% of control in the presence of 3.1 μmol/l of chlorpromazine, while the viability of unirradiated cells (UVA−) decreases below 70% in the presence of 25 μmol/l of chlorpromazine. Above data indicate that test compounds are safe for cosmetic and dermatological application including use with following exposure of treated skin with solar radiation.

TABLE 16

UVA-induced effects of test compounds on HaCaT viability

|  |  | 3.9 | 7.8 | 15.6 | 31.3 | 62.5 | 125 |
|---|---|---|---|---|---|---|---|
| 3 (µmol/l) | | | | | | | |
| −UVA | % control | 100.1 | 100.4 | 102.1 | 107.8 | 106.4 | 109.5 |
|  | SMODCH | 1.2 | 1.1 | 2.7 | 9.3 | 9.5 | 7.2 |
| +UVA | % control | 103.88 | 111.08 | 107.93 | 118.43 | 120.78 | 124.66 |
|  | SMODCH | 1.7 | 1.6 | 1.4 | 3.7 | 3.2 | 4.2 |
| 9 (µmol/l) | | | | | | | |
| −UVA | % control | 101 | 101.1 | 100.4 | 101.8 | 103.9 | 103.4 |
|  | SMODCH | 2.3 | 1.8 | 1 | 3.8 | 4.8 | 5.1 |
| +UVA | % control | 122.7 | 124.2 | 120.5 | 128.1 | 129.9 | 126.6 |
|  | SMODCH | 3.5 | 4.6 | 5.3 | 4.4 | 3.2 | 3.1 |
| 15 (µmol/l) | | | | | | | |
| −UVA | % control | 106.5 | 107.4 | 108.6 | 108.6 | 109.2 | 105 |
|  | SMODCH | 9.7 | 9.5 | 10.6 | 9.5 | 12.6 | 8.9 |
| +UVA | % control | 116.4 | 119.9 | 119.9 | 118.8 | 115.7 | 104 |
|  | SMODCH | 0.7 | 4.9 | 6.3 | 7.7 | 9 | 8.8 |
| 20 (µmol/l) | | | | | | | |
| −UVA | % control | 103.5 | 102.9 | 104.1 | 108.6 | 110.7 | 110.5 |
|  | SMODCH | 6.1 | 3.1 | 5.3 | 2.4 | 1.7 | 1.2 |
| +UVA | % control | 104.6 | 112.1 | 110.1 | 121.4 | 125.8 | 125.9 |
|  | SMODCH | 0.7 | 3.3 | 5.6 | 2.2 | 5.9 | 4.2 |

Example 14: In Vitro Test of Photoprotective Effects of Test Compounds on HaCaT Spontaneously Immortalized Aneuploid Human Keratinocyte Cell Line (HaCaT) was bought from CLS (Eppeheim, Germany) and used as an in vitro model. For all experiments the keratinocytes were seeded onto 96-well plates at a density of $1.6 \times 10^5$ cells/ml (0.2 ml per well) of growth medium (DMEM supplemented with fetal bovine serum (10%), penicillin (100 mg/ml) and streptomycin (100 U/ml)).

Test substances included compounds number 3, 9, 15 and 20. Compounds were dissolved in DMSO and then diluted in serum free medium (DMEM supplemented penicillin (100 mg/ml) and streptomycin (100 U/ml)). After 24 h incubation was growth medium changed to serum free medium containing test compounds. The final applied concentration range was 3.9-31.25 µmol/l. As a control, serum free medium supplemented with appropriate concentration of DMSO (0.5%, v/v) was used. Rosmarinic acid was used as positive control. After 60 minutes incubation with test compounds medium was discarded, cells were washed two-times with PBS and PBS supplemented with glucose (1 mg/ml) was applied. To study UVA photoprotection, a plate was exposed to a cytotoxic dose of UVA radiation (10 J/cm2) using a solar simulator SOL 500 (Dr. Hoenle Technology, Germany) equipped with a H1 filter transmitting wavelengths of 320-400 nm. To study UVB photoprotection, a plate was exposed to a cytotoxic dose of UVB radiation (150 mJ/cm2) using the solar simulator equipped with a H2 filter transmitting wavelengths of 295-320 nm. Intensity of UVA or UVB radiation was evaluated before each irradiation by UVA- or UVB-meter. Control (non-irradiated) plates were for the period of irradiation incubated in dark. After UVA or UVB exposure PBS with glucose was discarded and serum free medium was applied. After 24 hours (37° C., 5% CO2) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl2 (1%, m/v) in ratio 1:1 and then NR was dissolved in methanol (50%, v/v) with acetic acid (1%, v/v).

After 5 minutes of intensive shaking absorbance was measured at 540 nm. Experiments were performed in four independent repetitions with use of cells from four donors to minimize individual sensitivity of donor cells. Photoprotective effect was evaluated by comparison of experimental data (absorbance) of test compounds with a positive control and a negative control (according to the following equation:

$$\text{Protection (\%)} = 100 - \left| \frac{As - Anc}{Apc - Anc} \right| \cdot 100$$

As . . . absorbance of sample (cells pre-incubated with test compounds in serum free medium and irradiated)

Anc . . . absorbance of negative control (cells pre-incubated with s DMSO in serum free medium and non-irradiated=incubated in dark)

Apc . . . absorbance of positive control (cells pre-incubated with s DMSO in serum free medium and irradiated)

Results: Cells pre-incubated with test compound and exposed to UVA or UVB radiation showed higher viability (ability to incorporate NR) compared to those pre-incubated with DMSO (control) and UVA or UVB irradiated (Tab. 17 and 18). All test compounds showed higher or comparable photoprotective activity with rosmarinic acid used as positive control. Therefore test compound has high photoprotective potential.

TABLE 17

Photoprotective effects of test compounds and rozmarinic acid (positive control) on UVA-induced damage to HaCaT

|  | 3.9 | 7.8 | 15.6 | 31.3 |
|---|---|---|---|---|
| 3 (μmol/l) | | | | |
| Protection (%) | 26.8 | 34.3 | 46.0 | 50.7 |
| SMODCH | 6.9 | 9.7 | 6.9 | 6.1 |
| 9 (μmol/l) | | | | |
| Protection (%) | 72.1 | 70.3 | 66.8 | 61.4 |
| SMODCH | 4.4 | 4.9 | 8.1 | 10.0 |
| 15 (μmol/l) | | | | |
| Protection (%) | 41.2 | 56.9 | 55.3 | 76.7 |
| SMODCH | 5.5 | 7.8 | 1.7 | 9.7 |
| 20 (μmol/l) | | | | |
| Protection (%) | 12.3 | 25.0 | 28.9 | 31.6 |
| SMODCH | 5.2 | 7.7 | 10.2 | 9.1 |
| RA | | | | |
| Protection (%) | 23.6 | 42.3 | 36.2 | 44.0 |
| SMODCH | 7.2 | 7.4 | 12.0 | 16.0 |

TABLE 18

Photoprotective effects of test compounds and rozmarinic acid (positive control) on UVA-induced damage to HaCaT

|  | 3.9 | 7.8 | 15.6 | 31.3 |
|---|---|---|---|---|
| 3 (μmol/l) | | | | |
| Protection (%) | 27.3 | 46.5 | 47.8 | 53.8 |
| SMODCH | 4.4 | 11.6 | 14.4 | 14.4 |
| 9 (μmol/l) | | | | |
| Protection (%) | 48.8 | 56 | 55.7 | 56.5 |
| SMODCH | 1.9 | 12.6 | 7.7 | 6.3 |
| 15 (μmol/l) | | | | |
| Protection (%) | 12.3 | 35.3 | 37.8 | 51.3 |
| SMODCH | 7.7 | 12.6 | 7.5 | 3.5 |
| 20 (μmol/l) | | | | |
| Protection (%) | 45.7 | 66.2 | 64 | 75.2 |
| SMODCH | 7.1 | 1.6 | 3 | 10.3 |
| RA | | | | |
| Protection (%) | 22 | 48.5 | 55.7 | 54.3 |
| SMODCH | 0.4 | 1.2 | 2.2 | 13.1 |

Example 15: Markers of UVA Protection

Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. Fibroblasts were used between the 2nd and 4th passage. For all experiments the fibroblasts were seeded onto 6-well plates at a density of $0.5 \times 10^5$ cells/cm$^2$ of cultivation medium (DMEM supplemented with fetal calf serum (10%, v/v), penicillin (100 mg/ml) and streptomycin (100 U/ml)).

Test compounds included 6-(tetrahydrofuran-2-ylmethyl-amino)-9-(tetrahydrofuran-2-yl)purine and positive control (rosmarinic acid). Compounds were dissolved in DMSO and then diluted in serum free medium (DMEM supplemented with penicillin (100 mg/ml) and streptomycin (100 U/ml)). The final applied concentrations range was 2.5-20 μmol/l. As a control serum free medium supplemented with appropriate concentration of DMSO (0.5%, v/v) was used. Each test compound was in parallel applied on two 6-well plates with NHDF ($3.15 \times 10^5$ cells/cm$^2$). After 60 minutes incubation medium with test compound was discarded, cells were washed two-times with PBS and PBS supplemented with glucose (1 mg/ml) was applied. To study UVA photoprotection, a plate was exposed to a cytotoxic dose of UVA radiation (10 J/cm2) using a solar simulator SOL 500 (Dr. Hoenle Technology, Germany) equipped with a H1 filter transmitting wavelengths of 320-400 nm. Intensity of UVA radiation was evaluated before each irradiation by UVA-meter. Control (non-irradiated) plates were for the period of irradiation incubated in dark. After UVA exposure PBS with glucose was discarded and serum free medium was applied. After 1 hour (37° C., 5% CO2) cell damage was evaluated by analysis of reactive oxygen species (ROS) production. In parallel, intracellular levels of glutathion (GSH) were measured 4 hours (37° C., 5% CO2) after UVA application.

ROS Production

ROS production was evaluated by 2,7-Dichlorodihydro-fluorescein diacetate (H$_2$DCFDA). NHDF were incubated with (H$_2$DCFDA) (5 nmol/l, 20 min) 1 hour after UVA exposure. Subsequently, cells were washed two-times with PBS, scraped into PBS a sonicated. Samples were applied on 96-well plate and fluorescence was measured (488/525 nm) (INFINITE M200, Tecan, Switzerland) after centrifugation (10 000 rpm, 4° C., 10 min). Protein content was analyzed spectrophotometrically by bicinchoninic acid at 562 nm (INFINITE M200, Tecan, Switzerland).

GSH Depletion

GSH levels in NHDF were evaluated by reaction with 5,5'-Dithiobis(2-nitrobenzoic acid) (DTNB). Cells were washed two-times with PBS, scraped into acetic acid (1%, v/v) and sonicated. Samples were applied on 96-well plate after centrifugation (10 000 rpm, 4° C., 10 min) and reaction mixture was added (0.8 mol/l Tris/HCl, 20 mmol/l EDTA, pH 8.2; 20 mg/ml DTNB). Absorbance was measured at 412 nm. Protein content was analyzed spectrophotometrically by Lowry's method at 680 nm.

Activity of test compounds (not irradiated) in analyzed parameters were evaluated by comparison of experimental data according to the following equation:

$$\% \text{ of control} = 100 \cdot \left(\frac{(A_V - A_P)}{(A_K - A_P)}\right)$$

$A_P$ . . . background value
$A_V$ . . . sample value (cells pre-incubated with test compounds in serum free medium)
$A_K$ . . . control value (cells pre-incubated with s DMSO in serum free medium)

Photoprotective effect was evaluated by comparison of experimental data (absorbance, fluorescence) of test compounds with a positive control (cells pre-incubated with DMSO in serum free medium and irradiated) and a negative control (cells pre-incubated with DMSO in serum free medium and non-irradiated=incubated in dark) according to the following equation:

$$\text{Protection (\%)} = 100 - \left\{\left(\frac{(A_V - A_K)}{(A_{UV} - A_K)}\right) * 100\right\}$$

$A_K$ ... negative control value (DMSO in serum free medium and non-irradiated)

$A_{UV}$ ... positive control value (DMSO in serum free medium and irradiated)

$A_V$ ... sample value (cells pre-incubated with test compounds in serum free medium and irradiated)

Results: 6-(tetrahydrofuran-2-ylmethylamino)-9-(tetrahydrofuran-2-yl)purine did not showed negative effect on tested parameters (on non-irradiated cells) in test concentrations (2.5-20 µmol/l). Test compound protected cells against UVA-induced production of ROS as well as depletion of GSH (endogenous antioxidant) (Tab. 19 and 20) in a concentration-dependent manner. Compound 1 is more effective in protection against production of ROS but less effective in protection against GSH depletion in comparison with rosmarinic acid.

TABLE 19

Protective effect of 6-(tetrahydrofuran-2-ylmethylamino)-9-(tetrahydrofuran-2-yl)purine and rozmarinic acid (positive control) on UVA-induced ROS production

| Concentration (µmol/l) | 1 | RA |
|---|---|---|
| | ROS production Protection (%) | |
| 2.5 | 21.3 ± (6.9) | 20.6 ± (8.4) |
| 5 | 21.3 ± (5.2) | 24.1 ± (1) |
| 10 | 29.6 ± (3.3) | 24.1 ± (2.4) |
| 20 | 48.3 ± (0.5) | 30.3 ± (6.8) |

TABLE 20

Protective effect of 6-(tetrahydrofuran-2-ylmethylamino)-9-(tetrahydrofuran-2-yl)purine and rozmarinic acid (positive control) on UVA-induced GSH depletion

| Concentration (µmol/l) | 1 | RA |
|---|---|---|
| | GSH depletion Protection (%) | |
| 2.5 | 25.5 ± (6.8) | 53.9 ± (7.1) |
| 5 | 27.9 ± (7.2) | 42.8 ± (2.4) |
| 10 | 61.6 ± (15.7) | 68.6 ± (4.3) |
| 20 | 35.5 ± (14.1) | 50.5 ± (9) |

Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacky University, Olomouc and all patients signed written informed consent. Fibroblasts were used between the 2nd and 4th passage. For all experiments the fibroblasts were seeded onto 6-well plates at a density of $0.5 \times 10^5$ cells/cm$^2$ of cultivation medium (DMEM supplemented with fetal calf serum (10%, v/v), penicillin (100 mg/ml) and streptomycin (100 U/ml)).

Test compounds included 6-(tetrahydrofuran-2-ylmethylamino)-9-(tetrahydrofuran-2-yl)purine and positive control (rosmarinic acid). Compounds were dissolved in DMSO and then diluted in serum free medium (DMEM supplemented with penicillin (100 mg/ml) and streptomycin (100 U/ml)). The final applied concentrations range was 2.5-20 µmol/l. As a control serum free medium supplemented with appropriate concentration of DMSO (0.5%, v/v) was used. Each test compound was in parallel applied on two 6-well plates with NHDF ($3.15 \times 10^5$ cells/cm$^2$). After 60 minutes incubation medium with test compound was discarded, cells were washed two-times with PBS and PBS supplemented with glucose (1 mg/ml) was applied. To study UVB photoprotection, a plate was exposed to a cytotoxic dose of UVB radiation (150 mJ/cm2) using a solar simulator SOL 500 (Dr. Hoenle Technology, Germany) equipped with a H2 filter transmitting wavelengths of 295-320 nm. Intensity of UVB radiation was evaluated before each irradiation by UVB-meter. Control (non-irradiated) plated were for the period of irradiation incubated in dark. After UVB exposure PBS with glucose was discarded and serum free medium was applied. After 4 hours (37° C., 5% CO2) cell damage was evaluated by analysis of caspase-3 activity.

Caspase-3 Activity

Caspase-3 activity was evaluated by specific substrate (Ac-DEVD-AMC). NHDF were washed two-times with PBS, scraped into lysis buffer (50 mmol/l HEPES, pH 7.4; TritonX-100 (0.5%; v/v), protease inhibitor, 5 mmol/l DDT). Samples were applied on 96-well plate after centrifugation (10 000 rpm, 4° C., 10 min) and reaction buffer was added (20 mmol/l HEPES, pH 7.1, 2 mmol/l EDTA, protease inhibitor, 5 mmol/l DDT) cantaining specific substrate or inhibitors. Fluorescence was measured at (400/505 nm) after 1 hour incubation (37° C., dark). Protein content was analyzed spectrophotometrically by Bradford protein assay (INFINITE M200, Tecan, Switzerland).

$$\% \text{ of control} = 100 \cdot \left( \frac{(A_V - A_P)}{(A_K - A_P)} \right)$$

$A_P$ ... background value $A_V$ ... sample value (cells pre-incubated with test compounds in serum free medium)

$A_K$ ... control value (cells pre-incubated with s DMSO in serum free medium)

Photoprotective effect was evaluated by comparison of experimental data (absorbance, fluorescence) of test compounds with a positive control (cells pre-incubated with DMSO in serum free medium and irradiated) and a negative control (cells pre-incubated with DMSO in serum free medium and non-irradiated=incubated in dark) according to the following equation:

$$\text{Protection} (\%) = 100 - \left\{ \left( \frac{(A_V - A_K)}{(A_{UV} - A_K)} \right) * 100 \right\}$$

$A_K$ ... negative control value (DMSO in serum free medium and non-irradiated)

$A_{UV}$ ... positive control value (DMSO in serum free medium and irradiated)

$A_V$ ... sample value (cells pre-incubated with test compounds in serum free medium and irradiated)

Results: 6-(tetrahydrofuran-2-ylmethylamino)-9-(tetrahydrofuran-2-yl)purine did not showed negative effect on tested parameters (on non-irradiated cells) in test concentrations (2.5-20 µmol/l). Compound 1 decreased UVB-induced activity of caspase-3 (Tab. 21).

TABLE 21

Protective effect of 6-(tetrahydrofuran-2-ylmethylamino)-9-(tetrahydrofuran-2-yl)purine and rozmarinic acid (positive control) on UVB-induced caspase-3 activity

| Concentration (μmol/l) | Caspase-3 activity 1 | RA |
|---|---|---|
| | Protection (%) | |
| 2.5 | 41.2 ± (8.2) | 60.6 ± (3.1) |
| 5 | 84.4 ± (27.2) | 39.7 ± (13.1) |
| 10 | 71.1 ± (30.3) | 38.4 ± (5.9) |
| 20 | 45.9 ± (4.7) | 28.7 ± (3.8) |

Example 15: Comparative Gene Expression Analysis

Comparative gene expression analysis in human dermal fibroblast (HDF) was performed to gain insight into role of compound 1 in the photoprotection against UV-induced damage. Three independent HDF lines form three patients were treated with 5 μM 1 for 24 h or mock-treated with DMSO. Alternatively, the above three biological samples (without 1) were irradiated with UV light (5 J/cm2). 1.5-3.0×10$^6$ cells from each treatment or control was used for isolation of total RNA using trizol. cDNA sequencing libraries were prepared with the Illumina TruSeq Stranded mRNA LT Sample Prep Kit (Illumina, San Diego, Calif.) according to standard Illumina's protocols and sequenced on HiSeq 2500 apparatus (50 bp single-end reads).

Data were subjected to differential transcriptomic analysis with the aim to characterize significantly regulated genes and their expression levels. To reveal the molecular mechanism of the action of 1, we compared data from mock (DMSO)-treated HDF or UV-treated HDF with those obtained after 24 h treatment with 1. For data analysis, we performed ab initio method where sequencing reads were mapped to the reference genome. Comparison of the control group vs samples treated with 1 did not show any significantly regulated genes indicating 1 had low effect on the gene expression under normal conditions. Interestingly, when 1-treated group of data was compared with UV-treated group we could detect 1306 differentially regulated genes (P<0.05). 865 of those were upregulated and 441 genes were downregulated. To limit the number of genes that respond most significantly to 1 treatment we set relatively stringent conditions—we selected genes which $\log_2$ FC>1.5, or those with $\log_2$ FC<−1.5. Further inspection of the subgroups (41 upregulated genes and 41 downregulated, see Tab. 22 and Tab. 23, respectively) revealed major differences among those. In the group of the upregulated genes, we could observe a range of genes with regulatory, developmental or receptor/signaling function, such as the calcium sensing. These included calcium-activated potassium channel KCNN4, calcium sensor DYSF or calcium-dependent phospholipid-binding protein CPNE7. In addition, we noted increased expression of the negative regulator of reactive oxygen species NRROS and the scavenger cysteine-rich type 1 receptor CD163 that protects again oxidative damage suggesting that 1 facilitates a mechanism leading to the protection against damage caused by oxygen radicals. Thus, 1 seems to protect cells against oxidative damage caused primarily by UV-light or other stress conditions.

In contrast, in the group of the downregulated genes we found regulatory genes with a large group of genes that may be related to immune response. We observed upregulation of two chemokines, CCL8 and CXCL9, and cytokines TNFSF13B and TNFSF10. In addition, several protein kinases, such as HCK and JAK3, and innate immune response-related proteins TLR2 and GBP2 were found to be downregulated by 1. Hence, the immunosuppression mediated by 1 may contribute to the in vivo function of the compound.

TABLE 22

Genes upregulated in response to the treatment with the compound 1 (P ≤ 0.05 and $\log_2$FC > 1.5).

| Gene | Description | logFC |
|---|---|---|
| KIF1A | kinesin family member 1A | 3.05 |
| ANKRD33 | ankyrin repeat domain-containing protein 33 | 2.69 |
| HS3ST2 | heparan sulfate-glucosamine 3-sulfotransferase 2 | 2.50 |
| CHRNA9 | neuronal acetylcholine receptor subunit alpha-9 | 2.21 |
| TMEM233 | interferon-induced transmembrane domain-containing protein D2 | 2.12 |
| TM4SF1 | transmembrane 4 L6 family member 1 | 2.08 |
| SCG2 | secretogranin-2 | 2.00 |
| MYEOV | myeloma-overexpressed gene protein | 1.98 |
| PPP2R2C | serine/threonine-protein phosphatase 2A 55 kDa regulatory subunit B | 1.95 |
| KCNN4 | Intermediate conductance calcium-activated potassium channel 4 | 1.85 |
| RP11-184E9.1 | non-coding RNA | 1.78 |
| ITGA10 | integrin alpha-10 | 1.77 |
| CCL26 | C-C motif chemokine 26 | 1.75 |
| NRROS | negative regulator of reactive oxygen species | 1.74 |
| DYSF | dysferlin | 1.73 |
| ANGPTL4 | angiopoietin-related protein 4 | 1.73 |
| FAM81A | non-coding RNA | 1.71 |
| RP11-541M12.6 | non-coding RNA | 1.70 |
| RP11-367F23.2 | non-coding RNA | 1.70 |
| LINC00704 | non-coding RNA | 1.69 |
| FOLR3 | folate receptor gamma | 1.68 |
| CD163 | scavenger receptor cysteine-rich type 1 protein M130 | 1.67 |
| ARHGAP22 | rho GTPase-activating protein 22 | 1.66 |
| CYP51A1 | lanosterol 14-alpha demethylase | 1.65 |
| LINC01204 | non-coding RNA | 1.64 |
| CITED4 | cbp/p300-interacting transactivator 4 | 1.63 |
| RP11-54A9.1 | non-coding RNA | 1.63 |
| MET | MET proto-oncogene, receptor tyrosine kinase | 1.63 |
| EBF2 | transcription factor COE2 | 1.62 |
| CPNE7 | copine-7 | 1.61 |
| LINC00702 | non-coding RNA | 1.60 |
| TGM2 | protein-glutamine gamma-glutamyltransferase 2 | 1.58 |
| AC002456.2 | non-coding RNA | 1.58 |
| TMEM154 | transmembrane protein 154 | 1.57 |
| NUDT8 | nucleoside diphosphate-linked moiety X motif 8 | 1.56 |
| SLC20A1 | sodium-dependent phosphate transporter 1 | 1.56 |
| B4GALNT1 | beta-1,4-N-acetyl-galactosaminyltransferase 1 | 1.55 |
| STX1A | syntaxin-1A | 1.55 |
| CTD-2587H24.5 | non-coding RNA | 1.54 |
| ADGRG1 | adhesion G-protein coupled receptor G1 | 1.52 |
| CCDC107 | coiled-coil domain-containing protein 107 | 1.50 |

TABLE 23

Genes downregulated in response to the treatment with the compound 1 (P ≤ 0.05 and $\log_2$FC <−1.5).

| Gene | Description | logFC |
|---|---|---|
| RP11-383F6.1 | non-coding RNA | −1.50 |
| APOL6 | apolipoprotein L6 | −1.51 |
| RP11-400K9.4 | non-coding RNA | −1.51 |
| TMEM178A | transmembrane protein 178A | −1.52 |
| HAUS1P2 | non-coding RNA | −1.54 |

TABLE 23-continued

Genes downregulated in response to the treatment with the compound 1 (P ≤ 0.05 and log$_2$FC <−1.5).

| Gene | Description | logFC |
| --- | --- | --- |
| RORB | nuclear receptor ROR-beta | −1.57 |
| RP11-363H12.1 | non-coding RNA | −1.58 |
| SERPINB9 | serpin B9 | −1.59 |
| DHRS3 | short-chain dehydrogenase/reductase 3 | −1.60 |
| TP63 | tumor protein 63 | −1.61 |
| GBP2 | guanylate-binding protein 2 | −1.61 |
| TNFSF13B | tumor necrosis factor ligand superfamily member 13B | −1.61 |
| ADAMTS9-AS2 | non-coding RNA | −1.63 |
| TLR2 | toll-like receptor 2 | −1.63 |
| AC003986.6 | non-coding RNA | −1.65 |
| HCK | tyrosine-protein kinase HCK | −1.66 |
| GPR37L1 | G protein-coupled receptor 37 like 1 | −1.66 |
| JAK3 | tyrosine-protein kinase JAK3 | −1.68 |
| TNFRSF9 | tumor necrosis factor receptor superfamily member 9 | −1.68 |
| RP11-1100L3.8 | non-coding RNA | −1.70 |
| MOB3B | MOB kinase activator 3B | −1.70 |
| RP11-379B8.1 | non-coding RNA | −1.72 |
| BRINP2 | BMP/retinoic acid-inducible neural-specific protein 2 | −1.77 |
| IFIT2 | interferon-induced protein with tetratricopeptide repeats 2 | −1.77 |
| CXCL9 | C-X-C motif chemokine 9 | −1.79 |
| CLNS1AP1 | non-coding RNA | −1.80 |
| RNF150 | RING finger protein 150 | −1.80 |
| BTC | probetacellulin | −1.84 |
| FAM20A | pseudokinase FAM20A | −1.86 |
| RPL34P31 | non-coding RNA | −1.89 |
| BHLHE22 | class E basic helix-loop-helix protein 22 | −1.90 |
| FGD3 | FYVE, RhoGEF and PH domain-containing protein 3 | −1.93 |
| RP11-21C4.1 | non-coding RNA | −1.95 |
| CFB | complement factor B | −1.96 |
| RARRES3 | retinoic acid receptor responder protein 3 | −2.09 |
| TNFSF10 | tumor necrosis factor ligand superfamily member 10 | −2.14 |
| PSAT1P3 | non-coding RNA | −2.19 |
| KCNT2 | potassium channel subfamily T member 2 | −2.21 |
| RP1-181J22.1 | non-coding RNA | −2.53 |
| ABCG1 | ATP-binding cassette sub-family G member 1 | −2.63 |
| CCL8 | C-C motif chemokine 8 | −2.80 |

The invention claimed is:
1. Adenine derivatives of general formula I,

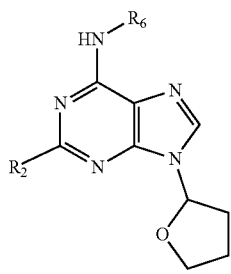

I and pharmaceutically acceptable salts thereof with alkali metals, ammonia, amines, or addition salts with acids, wherein
R2 is hydrogen or halogen; and
R6 is selected from a group containing
heteroaryl with 5- to 6-membered aromatic ring containing at least one heteroatom S whereas other ring atoms are carbon atoms, whereas the heteroaryl is unsubstituted or substituted by at least one substituent selected from the group consisting of C1-C4 alkyl, mercapto(C1-C4)alkyl, formyl, acetyl, halogen, carboxyl, amino, di(C1-C4)alkylamino and amino(C1-C4)alkyl;
heteroarylalkyl with 6-membered aromatic ring containing at least one heteroatom S whereas other atoms of the ring are carbon atoms, wherein the alkyl of the 6-membered heteroalkyl contains 1 to 4 carbon atoms, whereas the 6-membered heteroarylalkyl is unsubstituted or substituted by at least one substituent selected from the group C1-C4 alkyl, mercapto(C1-C4)alkyl, formyl, acetyl, halogen, carboxyl, amino, di(C1-C4)alkylamino and amino(C1-C4)alkyl;
heteroarylalkyl with 5-membered aromatic ring containing at least one heteroatom S whereas other atoms of the ring are carbon atoms, wherein the alkyl of the 5-membered heteroalkyl contains 1 to 4 carbon atoms, whereas the 5-membered heteroarylalkyl is unsubstituted or substituted by at least one substituent selected from the group C1-C4 alkyl, mercapto(C1-C4)alkyl, formyl, acetyl, halogen, carboxyl, amino, di(C1-C4)alkylamino and amino(C1-C4)alkyl;
heterocyclyl with 5- to 6-membered aliphatic ring containing at least one heteroatom selected from O and S whereas other atoms of the ring are carbon atoms, wherein the heterocycle is unsubstituted or substituted by at least one substituent selected from the group C1-C4 alkyl, mercapto(C1-C4)alkyl, formyl, acetyl, halogen, carboxyl, amino, di(C1-C4)alkylamino and amino(C1-C4)alkyl;
heterocyclylalkyl with 5- to 6-membered aliphatic ring containing at least one heteroatom selected from O and S whereas other atoms of the ring are carbon atoms, wherein the alkyl of the heterocyclylalkyl contains 1 to 4 carbon atoms, whereas the heterocyclylalkyl is unsubstituted or substituted by at least one substituent selected from the group C1-C4 alkyl, mercapto(C1-C4)alkyl, formyl, acetyl, halogen, carboxyl, amino, di(C1-C4)alkylamino, amino(C1-C4) alkyl; and
cycloalkylalkyl with ring containing 5 to 6 carbon atoms, wherein the alkyl of the cycloalkylalkyl contains 1 to 4 carbon atoms, whereas the cycloalkylalkyl is unsubstituted or substituted by at least one substituent selected from the group containing C1-C4 alkyl, mercapto(C1-C4)alkyl, formyl, acetyl, halogen, carboxyl, amino, di(C1-C4)alkylamino and amino(C1-C4)alkyl.
2. Adenine derivatives according to claim 1, selected from the group consisting of:
6-(tetrahydrofuran-2-ylmethylamino)-9-(tetrahydrofuran-2-yl)purine;
6-(5-methyltetrahydrofuran-2-ylmethylamino)-9-(tetrahydrofuran-2-yl)purine;
6-(1-tetrahydrofuran-2-ylethylamino)-9-(tetrahydrofuran-2-yl)purine;
6-(cyclopentylmethylamino)-9-(tetrahydrofuran-2-yl)purine;
6-(thiophen-2-ylmethylamino)-9-(tetrahydrofuran-2-yl)purine;
6-(3-methylthiophen-2-ylmethylamino)-9-(tetrahydrofuran-2-yl)purine;
6-(5-methylthiophen-2-ylmethylamino)-9-(tetrahydrofuran-2-yl)purine;

6-(5-chlorothiophen-2-ylmethylamino)-9-(tetrahydrofuran-2-yl)purine;
6-(5-bromothiophen-2-ylmethylamino)-9-(tetrahydrofuran-2-yl)purine;
6-(1-thiophen-2-ylethylamino)-9-(tetrahydrofuran-2-yl)purine;
2-chloro-6-(tetrahydrofuran-2-ylmethylamino)-9-(tetrahydrofuran-2-yl)purine;
2-chloro-6-(5-methyltetrahydrofuran-2-ylmethylamino)-9-(tetrahydrofuran-2-yl)purine;
2-chloro-6-(1-tetrahydrofuran-2-ylethylamino)-9-(tetrahydrofuran-2-yl)purine;
2-chloro-6-(thiophen-2-ylamino)-9-(tetrahydrofuran-2-yl)purine;
2-chloro-6-(thiophen-2-ylmethylamino)-9-(tetrahydrofuran-2-yl)purine;
2-chloro-6-(3-methylthiophen-2-ylmethylamino)-9-(tetrahydrofuran-2-yl)purine;
2-chloro-6-(5-methylthiophen-2-ylmethylamino)-9-(tetrahydrofuran-2-yl)purine;
2-chloro-6-(5-chlorothiophen-2-ylmethylamino)-9-(tetrahydrofuran-2-yl)purine;
2-chloro-6-(5-bromothiophen-2-ylmethylamino)-9-(tetrahydrofuran-2-yl)purine;
2-chloro-6-(1-thiophen-2-ylethylamino)-9-(tetrahydrofuran-2-yl)purine and
2-chloro-6-(cyclopentylmethylamino)-9-(tetrahydrofuran-2-yl)purine.

3. Adenine derivatives according to claim 1, wherein the substituent R6 is heteroaryl consisting of a 5-membered ring containing one heteroatom S, whereas the heteroaryl is unsubstituted or substituted by at least one substituent selected from the group containing C1-C4 alkyl, mercapto(C1-C4)alkyl, formyl, acetyl, halogen, carboxyl, amino, di(C1-C4)alkylamino and amino(C1-C4)alkyl.

4. Adenine derivatives according to claim 1, wherein the substituent R6 is heteroarylalkyl consisting of a 5-membered ring and C1-C2 alkyl, whereas the 5-membered ring contains one heteroatom S, while the heteroarylalkyl is unsubstituted or substituted by at least one substituent selected from the group containing C1-C4 alkyl, mercapto(C1-C4) alkyl, formyl, acetyl, halogen, carboxyl, amino, di(C1-C4) alkylamino and amino(C1-C4) alkyl.

5. Adenine derivatives according to claim 1, wherein the R6 substituent is heterocyclyl consisting of a 5-membered ring and the said 5-membered ring contains one heteroatom selected from O and S, while the heterocyclyl is unsubstituted or substituted by at least one substituent selected from the group comprising C1-C4 alkyl, mercapto(C1-C4)alkyl, formyl, acetyl, halogene, carboxyl, amino, di (C1-C4)alkylamino and amino(C1-C4) alkyl.

6. Adenine derivatives according to claim 1, wherein the substituent R6 is heterocyclylalkyl consisting of a 5-membered ring and C1-C2 alkyl, and the said 5-membered ring contains one heteroatom selected from O and S, whereas the heterocyclylalkyl is unsubstituted or substituted by at least one substituent selected from the group consisting of C1-C4 alkyl, mercapto(C1-C4)alkyl, formyl, acetyl, halogen, carboxyl, amino, di(C1-C4)alkylamino and amino(C1-C4) alkyl.

7. Adenine derivatives according to claim 1, wherein the substituent R6 is cyclopentylmethyl, which is unsubstituted or substituted by at least one substituent selected from the group comprising C1-C4 alkyl, mercapto(C1-C4)alkyl, formyl, acetyl, halogene, carboxyl, amino and di(C1-C4) alkylamino, amino(C1-C4)alkyl.

8. Cosmetic and/or therapeutic preparations, preparations for the protection of plants and/or preparations for the application to tissue cultures, which contain at least one compound of the general formula I according to claim 1.

* * * * *